US007928089B2

(12) United States Patent
Morton et al.

(10) Patent No.: US 7,928,089 B2
(45) Date of Patent: Apr. 19, 2011

(54) MUCOACTIVE AGENTS FOR TREATING A PULMONARY DISEASE

(75) Inventors: David Morton, Wiltshire (GB); David Ganderton, Wiltshire (GB); John Staniforth, Wiltshire (GB); Yorick Kamlag, Wiltshire (GB)

(73) Assignee: Vectura Limited, Chippenham, Wiltshire (GB)

( * ) Notice: Subject to any disclaimer, the term of this patent is extended or adjusted under 35 U.S.C. 154(b) by 450 days.

(21) Appl. No.: 10/571,184

(22) PCT Filed: Sep. 15, 2004

(86) PCT No.: PCT/GB2004/003932
§ 371 (c)(1),
(2), (4) Date: Jul. 17, 2006

(87) PCT Pub. No.: WO2005/025540
PCT Pub. Date: Mar. 24, 2005

(65) Prior Publication Data
US 2007/0065373 A1 Mar. 22, 2007

(30) Foreign Application Priority Data

Sep. 15, 2003 (GB) .................................. 0321611.6
Nov. 28, 2003 (GB) .................................. 0327723.3

(51) Int. Cl.
*A61K 31/727* (2006.01)
*C08B 37/10* (2006.01)
(52) U.S. Cl. ............................ 514/56; 536/21; 536/55.1
(58) Field of Classification Search .......................... None
See application file for complete search history.

(56) References Cited

U.S. PATENT DOCUMENTS

| 4,734,401 | A | | 3/1988 | Blouin |
| 5,145,684 | A | | 9/1992 | Liversidge |
| 5,254,330 | A | | 10/1993 | Ganderton |
| 5,296,471 | A | | 3/1994 | Holme |
| 5,399,363 | A | | 3/1995 | Liversidge |
| 5,464,817 | A | * | 11/1995 | Stossel et al. ................. 514/2 |
| 5,478,578 | A | | 12/1995 | Arnold |
| 5,607,662 | A | | 3/1997 | Baskeyfield |
| 5,668,118 | A | | 9/1997 | Kennedy |
| 5,690,910 | A | | 11/1997 | Ahmed |
| 5,696,100 | A | | 12/1997 | Holme |
| 5,707,974 | A | | 1/1998 | Kennedy |
| 5,780,014 | A | | 7/1998 | Eljamal |
| 5,804,594 | A | | 9/1998 | Murad |
| 5,851,453 | A | | 12/1998 | Hanna et al. .................. 264/5 |
| 5,874,063 | A | | 2/1999 | Briggner |
| 5,912,237 | A | | 6/1999 | Kennedy |
| 5,976,574 | A | | 11/1999 | Gordon |
| 5,980,865 | A | | 11/1999 | Ahmed |
| 5,985,248 | A | | 11/1999 | Gordon |
| 5,993,783 | A | | 11/1999 | Eljamal |
| 6,001,336 | A | | 12/1999 | Gordon |
| 6,019,968 | A | | 2/2000 | Platz |
| 6,027,714 | A | * | 2/2000 | Trofast ........................... 424/45 |
| 6,071,497 | A | | 6/2000 | Steiner |
| 6,075,013 | A | | 6/2000 | Weitz |
| 6,077,543 | A | | 6/2000 | Gordon |
| 6,077,683 | A | | 6/2000 | Kennedy |
| 6,116,237 | A | | 9/2000 | Schultz |
| 6,153,224 | A | | 11/2000 | Staniforth |
| 6,193,957 | B1 | | 2/2001 | Ahmed |
| 6,221,338 | B1 | | 4/2001 | Staniforth |
| 6,223,455 | B1 | | 5/2001 | Chickering, III |
| 6,257,233 | B1 | | 7/2001 | Burr et al. ................. 128/203.15 |
| 6,258,341 | B1 | | 7/2001 | Foster |
| 6,284,287 | B1 | | 9/2001 | Sarlikiotis |
| 6,308,434 | B1 | | 10/2001 | Chickering |
| 6,309,671 | B1 | | 10/2001 | Foster |
| 6,365,190 | B1 | | 4/2002 | Gordon |
| 6,369,115 | B1 | | 4/2002 | Ward |
| 6,372,258 | B1 | * | 4/2002 | Platz et al. .................... 424/489 |
| 6,384,021 | B1 | | 5/2002 | Mardiguian |
| 6,423,344 | B1 | | 7/2002 | Platz |
| 6,428,771 | B1 | | 8/2002 | Steiner |
| 6,475,523 | B1 | | 11/2002 | Staniforth |
| 6,518,239 | B1 | * | 2/2003 | Kuo et al. ......................... 514/2 |
| 6,521,260 | B1 | | 2/2003 | Staniforth |
| 6,560,897 | B2 | | 5/2003 | Chickering |
| 6,572,893 | B2 | | 6/2003 | Gordon |
| 6,576,264 | B1 | | 6/2003 | Henriksen |
| 6,582,678 | B2 | | 6/2003 | Staniforth |

(Continued)

FOREIGN PATENT DOCUMENTS

CN 1546063 6/2006

(Continued)

OTHER PUBLICATIONS

Dunbar et al., "Evaluation of Atomizer Performance in Production of Respirable Spray-Dried Particles" Pharmaceutical Development and technology (1998) vol. 3 No. 4, pp. 433-441.*
2006 Chemical Abstracts Catalog, published 2006 by Chemical Abstracts Service, p. 52.*
Lee, M. M., et al. "Effect of low molecular weight (MW) heparin on the elasticity of dog mucus" Clinical and Investigative Medicine No. Suppl., 1998, p. S102 XP009039322.
Lee, M. M., et al. "Mucociliary Clearance Increase Due to Low Molecular Weight (LMW) Heparin" Pediatr. Pulmonol, No. S17, 1998, p. 386 XP000903996.
Communication pursuant to Rule 114(2) EPC issued in connection with corresponding European Patent Application No. 04768478.2-2123.

(Continued)

*Primary Examiner* — Eric S Olson
(74) *Attorney, Agent, or Firm* — Davidson, Davidson & Kappel, LLC

(57) ABSTRACT

The present invention relates to mucoactive agents, such as heparin which are useful in the treatment of diseases where excess mucus is present in the respiratory tract, such as cystic fibrosis and chronic obstructive pulmonary disease. In particular, the invention relates to pharmaceutical compositions for administration by pulmonary inhalation. It also relates to methods for producing particles suitable for pulmonary inhalation, such as spray drying or jet milling.

42 Claims, 2 Drawing Sheets

U.S. PATENT DOCUMENTS

| | | | |
|---|---|---|---|
| 6,585,959 B2 | 7/2003 | Walz | |
| 6,589,560 B2 | 7/2003 | Foster | |
| 6,592,904 B2 | 7/2003 | Platz | |
| 6,635,283 B2 | 10/2003 | Edwards | |
| 6,641,844 B1 | 11/2003 | Musa | |
| 6,673,335 B1 * | 1/2004 | Platz et al. | 424/45 |
| 6,780,508 B1 | 8/2004 | Caponetti | |
| 6,797,258 B2 | 9/2004 | Platz | |
| 6,811,767 B1 | 11/2004 | Bosch | |
| 6,835,372 B2 | 12/2004 | Kuo | |
| 6,848,197 B2 | 2/2005 | Chen | |
| 6,884,794 B2 | 4/2005 | Staniforth | |
| 6,905,239 B2 | 6/2005 | Boeck | |
| 6,918,991 B2 | 7/2005 | Chickering | |
| 6,921,458 B2 | 7/2005 | Chickering | |
| 6,921,527 B2 | 7/2005 | Platz | |
| 6,926,911 B1 | 8/2005 | Boucher, Jr. | |
| 6,933,372 B2 | 8/2005 | Raghavan | |
| 6,962,006 B2 | 11/2005 | Chickering | |
| 6,969,705 B2 | 11/2005 | Pecquet et al. | |
| RE38,912 E | 12/2005 | Walz | |
| 6,974,593 B2 | 12/2005 | Henriksen | |
| 6,989,155 B1 | 1/2006 | Ganderton | |
| 6,994,842 B2 | 2/2006 | Lee | |
| 7,011,818 B2 | 3/2006 | Staniforth | |
| 7,132,115 B2 | 11/2006 | Musa | |
| 7,138,141 B2 | 11/2006 | Platz | |
| 7,223,748 B2 | 5/2007 | Staniforth | |
| 7,229,607 B2 | 6/2007 | Bannister | |
| 7,244,414 B2 | 7/2007 | Boeck | |
| 7,267,813 B2 | 9/2007 | Watanabe | |
| 7,344,734 B2 | 3/2008 | Heijerman | |
| 7,368,104 B2 | 5/2008 | Bannister | |
| 7,399,528 B2 | 7/2008 | Caponetti | |
| 7,469,488 B2 | 12/2008 | Chen | |
| 7,521,068 B2 | 4/2009 | Bosch | |
| 7,541,022 B2 | 6/2009 | Staniforth | |
| 7,560,444 B2 | 7/2009 | Richardson | |
| 7,575,761 B2 | 8/2009 | Bennett | |
| 7,666,395 B2 | 2/2010 | Boucher, Jr. | |
| 2001/0007665 A1 | 7/2001 | Illum | |
| 2001/0046974 A1 | 11/2001 | Weitz | |
| 2001/0055639 A1 | 12/2001 | Moritz | |
| 2002/0010152 A1 | 1/2002 | De Ambrosi | |
| 2002/0081266 A1 | 6/2002 | Woolfe | |
| 2002/0099023 A1 | 7/2002 | Boucher | |
| 2002/0127188 A1 | 9/2002 | Platz | |
| 2002/0128225 A1 | 9/2002 | Liu | |
| 2003/0017211 A1 | 1/2003 | Steiner | |
| 2003/0086877 A1 | 5/2003 | Platz | |
| 2003/0091513 A1 | 5/2003 | Mohsen | |
| 2003/0113272 A1 | 6/2003 | Staniforth | |
| 2003/0118514 A1 | 6/2003 | Larhrib | |
| 2003/0124087 A1 | 7/2003 | Kim | |
| 2003/0124193 A1 | 7/2003 | Snyder | |
| 2003/0147848 A1 | 8/2003 | Geng | |
| 2003/0162835 A1 | 8/2003 | Staniforth | |
| 2003/0165436 A1 | 9/2003 | Staniforth | |
| 2003/0166509 A1 | 9/2003 | Edwards | |
| 2003/0175214 A1 | 9/2003 | Staniforth | |
| 2003/0180755 A1 | 9/2003 | Hwang | |
| 2003/0186271 A1 | 10/2003 | Hwang | |
| 2003/0198601 A1 | 10/2003 | Platz | |
| 2003/0202944 A1 | 10/2003 | Staniforth | |
| 2003/0203036 A1 | 10/2003 | Gordon | |
| 2003/0215512 A1 | 11/2003 | Foster | |
| 2004/0009127 A1 | 1/2004 | Musa | |
| 2004/0028746 A1 | 2/2004 | Svenson | |
| 2004/0037785 A1 | 2/2004 | Staniforth | |
| 2004/0043064 A1 | 3/2004 | Iorio | |
| 2004/0047810 A1 | 3/2004 | Staniforth | |
| 2004/0062719 A1 | 4/2004 | Buckton | |
| 2004/0071635 A1 | 4/2004 | Staniforth | |
| 2004/0096403 A1 | 5/2004 | Steiner | |
| 2004/0101482 A1 | 5/2004 | Sanders | |
| 2004/0105821 A1 | 6/2004 | Bernstein | |
| 2004/0109827 A1 | 6/2004 | Onoue | |
| 2004/0121003 A1 * | 6/2004 | Chickering et al. | 424/465 |
| 2004/0136904 A1 | 7/2004 | Pitcairn | |
| 2004/0175328 A1 | 9/2004 | Sutton | |
| 2004/0241232 A1 | 12/2004 | Brown | |
| 2005/0003004 A1 | 1/2005 | Vehring | |
| 2005/0013867 A1 | 1/2005 | Lehrman | |
| 2005/0019270 A1 | 1/2005 | Finlay | |
| 2005/0019411 A1 | 1/2005 | Colombo | |
| 2005/0032745 A1 | 2/2005 | Weitz | |
| 2005/0048127 A1 | 3/2005 | Brown | |
| 2005/0123509 A1 | 6/2005 | Lehrman | |
| 2005/0152849 A1 | 7/2005 | Staniforth | |
| 2005/0158249 A1 | 7/2005 | Edwards | |
| 2005/0170004 A1 | 8/2005 | Rosenberger | |
| 2005/0201948 A1 | 9/2005 | Ellison | |
| 2005/0209099 A1 | 9/2005 | Chickering | |
| 2005/0211244 A1 | 9/2005 | Nilsson | |
| 2005/0220720 A1 | 10/2005 | Edwards | |
| 2005/0282771 A1 | 12/2005 | Johnson | |
| 2005/0282775 A1 | 12/2005 | Kennedy | |
| 2006/0014698 A1 | 1/2006 | O'Connor | |
| 2006/0025326 A1 | 2/2006 | Lankinen | |
| 2006/0029552 A1 | 2/2006 | Staniforth | |
| 2006/0078622 A1 | 4/2006 | Majuru | |
| 2006/0078623 A1 | 4/2006 | Dhoot | |
| 2006/0088479 A1 | 4/2006 | Whitfield | |
| 2006/0188451 A1 | 8/2006 | Lee | |
| 2006/0191375 A1 | 8/2006 | Feldstein | |
| 2006/0199009 A1 | 9/2006 | Anderson | |
| 2006/0199010 A1 | 9/2006 | DiCarlo | |
| 2006/0257491 A1 | 11/2006 | Morton | |
| 2006/0292081 A1 * | 12/2006 | Morton et al. | 424/46 |
| 2006/0292083 A1 | 12/2006 | Zeng | |
| 2006/0292224 A1 | 12/2006 | Moore | |
| 2007/0020199 A1 | 1/2007 | Platz | |
| 2007/0081948 A1 | 4/2007 | Morton | |
| 2007/0098803 A1 | 5/2007 | Dobbs | |
| 2007/0152361 A1 | 7/2007 | Hansen | |
| 2007/0166386 A1 | 7/2007 | Chinea | |
| 2007/0190158 A1 | 8/2007 | Hwang | |
| 2007/0287675 A1 | 12/2007 | Hitt | |
| 2007/0298116 A1 | 12/2007 | Bechtold-Peters | |
| 2008/0031824 A1 | 2/2008 | Smyth | |
| 2008/0038359 A1 | 2/2008 | Abu-Izza | |
| 2008/0050444 A1 | 2/2008 | Taneja | |
| 2008/0050592 A1 | 2/2008 | Fiannaca | |
| 2008/0057129 A1 | 3/2008 | Lerner | |
| 2008/0119438 A1 | 5/2008 | Weitz | |
| 2008/0125393 A1 | 5/2008 | DeAngelis | |
| 2008/0127972 A1 | 6/2008 | Morton | |
| 2008/0131518 A1 | 6/2008 | Zeng | |
| 2008/0181957 A1 | 7/2008 | Wei | |
| 2008/0181958 A1 | 7/2008 | Rothrock | |
| 2008/0220073 A1 | 9/2008 | Bannister | |
| 2008/0254127 A1 | 10/2008 | Watanabe | |
| 2008/0299210 A1 | 12/2008 | Wei | |
| 2008/0306022 A1 | 12/2008 | Miyamoto | |
| 2008/0317863 A1 | 12/2008 | Nystrom | |
| 2009/0068274 A1 | 3/2009 | Edwards | |
| 2009/0117193 A1 | 5/2009 | Kuo | |
| 2009/0186088 A1 | 7/2009 | Chan | |
| 2009/0203789 A1 | 8/2009 | Clement | |
| 2009/0208581 A1 | 8/2009 | Edwards | |
| 2009/0264389 A1 | 10/2009 | Zeng | |
| 2009/0269411 A1 | 10/2009 | Bellinghausen | |
| 2009/0269412 A1 | 10/2009 | Staniforth | |
| 2009/0312380 A1 | 12/2009 | Becker | |
| 2010/0015238 A1 | 1/2010 | Mueller-Walz | |
| 2010/0034910 A1 | 2/2010 | Bennett | |
| 2010/0055192 A1 | 3/2010 | Musa | |
| 2010/0055194 A1 | 3/2010 | Majuru | |

FOREIGN PATENT DOCUMENTS

| | | |
|---|---|---|
| GB | 2322326 | 8/1998 |
| GB | 2353222 | 2/2001 |
| WO | WO 92/18544 | 10/1992 |
| WO | WO 92/19249 | 11/1992 |
| WO | 94 02107 | 2/1994 |
| WO | WO 94/02107 | 2/1994 |
| WO | 95 01221 | 1/1995 |

| WO | 95 01324 | 1/1995 |
| WO | 96 00610 | 1/1996 |
| WO | 96 23485 | 8/1996 |
| WO | 97 03649 | 2/1997 |
| WO | WO 97/41833 | 11/1997 |
| WO | 98 04133 | 2/1998 |
| WO | WO 98/42749 | 10/1998 |
| WO | 99 01141 | 1/1999 |
| WO | 99 06025 | 2/1999 |
| WO | WO 99/06025 | 2/1999 |
| WO | WO 99/07340 | 2/1999 |
| WO | WO 99/52506 | 10/1999 |
| WO | 0033811 | 6/2000 |
| WO | WO 00/33789 | 6/2000 |
| WO | WO 00/44367 | 8/2000 |
| WO | 01 00262 | 1/2001 |
| WO | WO 01/00312 | 1/2001 |
| WO | 01 15672 | 3/2001 |
| WO | WO 01/32144 | 5/2001 |
| WO | WO 01/34232 | 5/2001 |
| WO | WO 01/78696 | 10/2001 |
| WO | 02 43701 | 6/2002 |
| WO | WO 03/035790 | 5/2003 |
| WO | 03 068187 | 8/2003 |
| WO | 03 068188 | 8/2003 |
| WO | 03 068254 | 8/2003 |
| WO | WO 03/068187 | 8/2003 |
| WO | WO 03/068188 | 8/2003 |
| WO | WO 2004/017942 | 3/2004 |
| WO | WO 2005/010051 | 2/2005 |
| WO | WO 2005/089717 | 9/2005 |
| WO | 2006/008173 | 1/2006 |
| WO | WO 2006/055950 | 5/2006 |
| WO | WO 2006/130943 | 12/2006 |
| WO | WO 2007/011989 | 1/2007 |
| WO | WO 2007/094829 | 8/2007 |
| WO | WO 2008/055951 | 5/2008 |
| WO | WO 2008/058691 | 5/2008 |
| WO | WO 2008/066810 | 6/2008 |
| WO | WO 2008/067868 | 6/2008 |
| WO | WO 2008/134817 | 11/2008 |
| WO | WO 2009/001064 | 12/2008 |
| WO | WO 2009/050217 | 4/2009 |

OTHER PUBLICATIONS

Lucas, Paul, et al., "Enhancement of small particle size dry powder aerosol formulations using an ultra low density additive", Pharmaceutical Research, vol. 16, No. 10, pp. 1643-1647 1999.

Tomkiewicz, R.P., et al., "A comparison of new mucolytic N-acetylcysteine L-lysinate with N-acetylcysteine: airway epithelial function and mucus changes in dog", Pulmonary Pharmacology, 8, pp. 259-265, 1995.

Tomkiewicz, R.P., et al., "Mucolytic treatment with N-acetylcysteine L-lysinate metered dose inhaler in dogs: airway epithelial function changes", Eur. Respir J., 7, pp. 81-87, 1994.

Wuropean Patent Office's Summons to Oral Proceedings dated Dec. 20, 2010 issued in connection with corresponding European Patent Application No. 04768478.2.

Japanese Office Action dated Dec. 14, 2010.

* cited by examiner

FIG. 1

Therapeutic mist

Piezo-electric crystal

High frequency source

FIG. 2

Ultrasonic Nebulizer

Hot air (500C)

Flexible tubing

Filter

Pump

MUCOACTIVE AGENTS FOR TREATING A PULMONARY DISEASE

CROSS-REFERENCE TO RELATED APPLICATIONS

This application is a national stage application of PCT international application PCT/GB04/03932, filed Sep. 15, 2004, which claims priority to foreign applications GB0321611.6, filed Sep. 15, 2003, and GB0327723.3, filed Nov. 28, 2003.

FIELD OF THE INVENTION

The present invention relates to pharmaceutical compositions which are useful in the treatment of diseases where excess mucus is present in the respiratory tract, such as cystic fibrosis and chronic obstructive pulmonary disease. In particular, the invention relates to pharmaceutical compositions for administration by pulmonary inhalation.

BACKGROUND

Mucus is a viscous gel, the properties of which are dependent on a variety of factors. Mucus is primarily made up of a mixture of variable amounts of mucous glycoproteins, water, low molecular weight ions, proteins and lipids. These components interact in a number of ways and these interactions create the three-dimensional structure of the gel and determine the gel's viscosity and elasticity.

Mucin is the principle polymeric component of the mucus gel and consists of a peptide backbone with glycosylated and non-glycosylated domains and oligosaccharide chains. The presence of sulphated and sialic terminals makes the molecule highly polyanionic. The mucins form a polydisperse group of densely charged linear polymers, some of which are up to 6 μm in length, with random tangles. The theological properties are mainly dependent on the tangle density, which in turn is determined by the degree of mucus hydration and mucin molecule length. The necrotic activated neutrophils release large amounts of DNA, actin and proteins which also polymerise and interact with mucin. This process considerably increases the tangle density to form highly viscoelastic mucus gels.

A variety of different types of bonds within airway mucus affect the chemical and physical properties of the mucus, such as viscoelasticity. Disulphide bonds are covalent bonds which link glycoprotein subunits into the large, extended macromolecular chains known as mucins. Cross-links form between adjacent mucin polymers, probably as a result of their large size. The sugar units, which make up the oligosaccharide side-chains and account for about 80% of the mucin weight, form hydrogen bonds with complimentary units on neighbouring mucins. Although each individual bond is weak and readily dissociates, there are very large numbers of bond sites, making this a significant type of bonding within the mucus. In addition, mucins are also ionized, containing both positively charged amino acid residues as well as negatively charged sugar units, principally sialic acid and sulphated residues. The degree of mucin ionisation may actually increase in airway disease. For example, in cystic fibrosis (CF) the proportion of sulphated residues is further elevated because of alterations in glycosyl transferase activities within the Golgi apparatus. The ionic interactions between fixed negative charges result in a stiffer, more extended macromolecular conformation, effectively increasing the polymer size and adding to the numbers of entanglements. Finally, in airway diseases characterized by infection and inflammation, such as CF, high molecular weight DNA and actin filaments are released by dying leukocytes, and exopolysaccharides are secreted by bacteria. These add further bonding and bulk to the mucus.

Mucus is a critical component of the primary defence mechanism of the respiratory tract, trapping inhaled particulate and microbial material for removal via the mucociliary system. However, when this mechanism fails to clear sufficiently, mucus accumulates and must be coughed up as sputum, otherwise it is retained in the respiratory tract and can encourage the colonisation by microorganisms which may lead to chronic lung inflammation and obstruction.

Retention of the mucus in the respiratory tract presents a particular problem as it not only obstructs the airways but also facilitates infection and promotes a self-perpetuating cycle of infection and inflammation. Pathological agents such as bacteria (e.g. Pseudomonas aeruginosa) are often able to establish colonies within the mucus.

Problems tend to arise when the initial bacterial infection stimulates neutrophil chemotaxis, but the neutrophils are unable to effectively clear. Defective neutrophil apoptosis and impaired phagocytosis are key factors in the pathogenesis of lung disease in CF. Neutrophil proteases and oxidants are released during the process and these have a number of effects. They cause both cellular damage and impairment of ciliary movement. They are also potent secretagogues and actually enhance further mucus secretion. The proteases also cleave anti-proteases and cell surface markers, further impairing the host defence mechanisms. Thus, the cycle is perpetuated as these effects further impair mucus clearance at the same time as increasing mucus secretion, encouraging bacterial stasis and promoting airway inflammation. Therefore, the failure of the neutrophils to clear the original infection actually leads to a rapid deterioration of the situation and the process accounts for much of the morbidity and mortality observed in patients with CF.

There are two main causes of mucus retention. The first is airway mucus hypersecretion, where the body produces and secretes elevated levels of mucus and the mucociliary system is unable to cope with and clear the large amounts of mucus quickly enough. The second cause is where the mucus has abnormal viscoelasticity. Where the mucus has an unusually high viscoelasticity, it is much more difficult for the mucociliary system to move the mucus and clear it from the airways.

Agents which affect the mucus in a way that assists clearance have traditionally been referred to as "mucolytics" agents. However, this term may be inaccurate, as may of the agents in question do not exert their effect on the mucus by lysis. Therefore, agents which assist mucus clearance are herein referred to as mucoactive agents.

Classical courses of action taken to treat individuals afflicted with airway hypersecretion and/or abnormal mucus viscoelasticity include antibiotic therapy, administration of bronchiodilators, use of systemic or inhaled corticosteroids, or oral administration of expectorants for liquefaction of the mucus. It is also known to treat the sufferers with aerosol delivered "mucolytic" agents, such as water and hypertonic saline solution. Recombinant human DNase I (rhDNase) has been used to treat CF sufferers. The rhDNase is thought to enzymatically digest the naked DNA released into the airway surface fluid from bacteria, neutrophils, and other cellular debris. It is this DNA which is thought to contribute to the elevated viscoelasticity of the mucus in CF sufferers.

However, these conventional approaches have met with only limited success and there is the need for cheap and effective treatment for mucus retention in the lungs. What is more, it is an aim of the present invention to provide a treatment which will lead to a reduction in the mucus elasticity and viscosity and which will result in improved cough and airway clearance of the mucus and also enable clearance by means of ciliary action.

Agents such as rhDNase, which digests the naked DNA in the mucus, and gelsolin, which digests actin in the mucus, have been shown to affect the elasticity components of the network, as opposed to the viscosity. In model studies, this will tend to improve cough and airway clearance, rather than helping clearance by means of ciliary action.

It has been suggested that agents which disrupt the cross-links in the mucus cause a reduction in both elasticity and viscosity. This is the preferred result, as it will lead to an improvement in ciliary clearance, according to model studies.

Dextrans have been identified as being a potentially useful agent for improving mucus clearance in International Publication No. WO 99/01141. In this patent application, it is suggested, from in vitro models, that dextrans decrease mucus viscoelasticity and increase mucociliary clearability. The dextrans are thought to have this effect by disrupting the hydrogen bonding between mucins within the three-dimensional mucus structure. It is hypothesised that the dextrans compete with the mucin for the hydrogen bonding sites, resulting in the substitution, by dextran carbohydrate moieties, of oligosaccharide moieties linked to high molecular weight mucin peptides that make up the mucus gel. The dextrans used have significantly lower molecular weight and so these new hydrogen bonds are structurally and rheologically ineffective, thus reducing the overall cross-link density within the mucus and this, it is believed, improves mucus clearance by ciliary and cough mechanisms.

In a later patent application, International Publication No. WO 01/15672, it is further suggested that the action of dextrans may be further enhanced by using charged forms. A charged dextran, for example dextran sulphate, is thought to have dual activity. Firstly, it is said to have the effects due to competition for hydrogen bonding sites as discussed above. Secondly, the ionic nature of the charged dextran is thought to have an additional effect, shielding some of the fixed charges along the macromolecular core of the mucin polymer, making it less stiff and reducing the number of entanglement cross-links with neighbouring macromolecules within the mucus and thereby reducing viscoelasticity due to ionic interactions.

In WO 01/15672, it is also suggested that the charged oligosaccharide heparin is not suitable for treating pulmonary diseases such as CF, because it is expensive to produce and, more significantly, because it could potentially have toxic side-effects such as pulmonary haemoptysis, which is bleeding of the tracheobronchial mucosa.

Heparin is a linear polysaccharide which, along with related proteoglycans such as heparan sulphate, is a member of the group of macromolecules referred to as glycosaminoglycans. Owing to their linear anionic polyelectrolyte structure, these macromolecules are involved in various biological processes. While heparin has been used largely for its anticoagulant effects based on its binding to plasma antithrombin III, there is evidence that heparin and other glycosaminoglycans also possess various anti-inflammatory and immunoregulatory properties, including the modulation of T-lymphocytes, complement activation, inhibition of neutrophil chemotaxis, smooth muscle growth and reduction of intrinsic DNA viscosity.

Heparin is a heterogeneous mixture of variably sulphated polysaccharide chains with a molecular weight range of 6000 to 30,000 Daltons. Whole or unfractionated heparin (UFH) may be fractionated to give low and high molecular weight fractions, as is well known in the art. Fractionated, low molecular weight heparin (LMWH) has been shown to reduce the viscoelasticity of dog mucus and improve mucociliary clearance on a frog palate model.

The effects of inhaling an aqueous solution of heparin using a nebuliser on bronchial asthma have been the subject of several studies. However, the results of these studies have been inconsistent, possibly because of the difficulty in quantifying the dosages of inhaled heparin reaching the lower respiratory tract.

N-acetyl-L-cysteine, which is also commonly called acetylcysteine or NAC, is a chemical produced by the body that enhances the production of the enzyme glutathione, a powerful antioxidant. NAC is known to be a mucactive agent and is used to help break up the thick mucus often present in people suffering from chronic respiratory ailments. It is available in an oral solution as Mucomyst (trade mark) that can be ingested or aerosolised and inhaled.

SUMMARY OF THE INVENTION

Whilst the prior art discusses the possibility of combining hydrogen bond competition and ionic shielding in order to provide a two-fold mode of reducing mucus viscoelasticity, there are even further mechanisms by which the viscoelasticity may be reduced and the present invention seeks to use these other mechanisms to provide an even more efficient means for assisting mucus clearance, especially in patients suffering from conditions such as cystic fibrosis (CF), chronic obstructive pulmonary disease (COPD), chronic bronchitis, acute asthma, or bronchiectasis.

Mucus clearance can be improved by reducing the viscosity and elasticity of the mucus gel. There are a number of mechanisms by which these properties can be affected to assist clearance, by coughing, by ciliary movement or a by combination of the two.

BRIEF DESCRIPTION OF THE DRAWINGS

FIG. 1 How USN works

FIG. 2 Schematic Drawing of Ultrasonic Set-up

DETAILED DESCRIPTION

Figure 3:
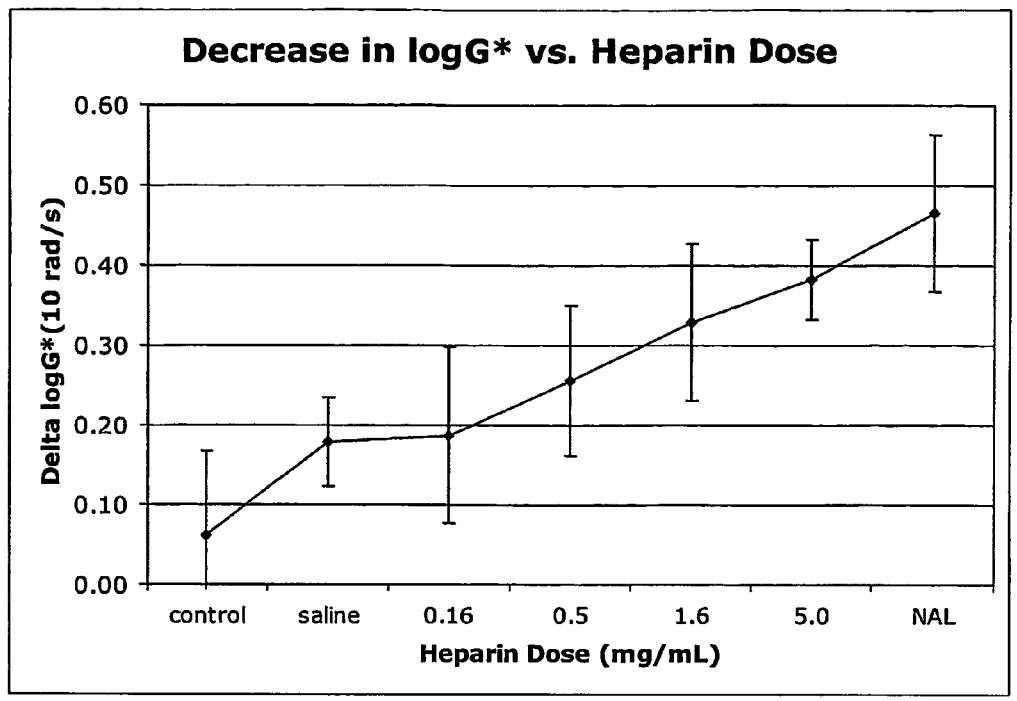
FIG. 3 Graph showing the dose-response curve for administration of heparin to CF sputum samples, as measured by the decrease in G* (vector sum of viscosity and elasticity of sputum).

Firstly, the cross-links within the mucus gel structure can be disrupted. This can be achieved by agents which break the di-sulphide bonds between the glycoproteins within the mucus. Alternatively or additionally, the cross-links within the mucus gel structure may be disrupted by agents which compete for hydrogen bonding sites, as described above in relation to dextran. Furthermore, the ionic bonding which exists within the gel can also be disrupted, by shielding the charges using an ionic agent. This has been described in connection with the use of a charged dextran.

Secondly, the mucus may be diluted by increasing its water content. This will reduce the gel's viscosity and will ease mucus clearance. This may be done by administering an agent to the mucus which will draw water into the mucus by exerting an osmotic effect. Alternatively, the water content of the mucus may be increased by agents which control sodium channels in the lung epithelium and are therefore able to block the uptake of salt and water across the airway epithelium.

Thirdly, digestion of the naked DNA and other cellular debris, such as filamentous actin, found in the mucus will also reduce the viscosity and elasticity of the mucus.

Thus, in a first aspect of the present invention, a composition for assisting mucus clearance is provided, the composition comprising one or more mucoactive agents for reducing cross-linking within the mucus; for diluting the mucus; and/or for digesting naked DNA and cell debris within the mucus.

The compositions according to the invention are preferably administered directly to the lung by inhalation. The mucoactive agents have a local effect on the mucus in the lungs. These agents are not intended to have a systemic effect and they are not intended to be absorbed into the bloodstream via the lung.

In a preferred embodiment of the invention, the composition comprises two or more mucoactive agents and has at least two of the listed effects on the mucus.

Preferably, the composition according to the invention further has the effect of reducing inflammation.

In one embodiment of the present invention, the composition comprises one or more mucoactive agents together with an additional active agent. The additional active agent may be an agent which has a therapeutic effect which will assist in the treatment of the underlying cause or the symptoms of the conditions involving airway hypersecretion and/or abnormal mucus viscoelasticity. Alternatively, the additional active agent may be included to treat or prevent a different condition.

In a particularly preferred embodiment, the additional active agent is an anti-inflammatory agent, such as one of the anti-inflammatory agents listed below. The composition may therefore, for example, comprise a combination of NAC and ibuprofen.

In another embodiment of the invention, the mucoactive agent for reducing the cross-linking within the mucus is an agent which has hydrogen bonding sites which compete with the hydrogen bonding sites of the side-chains of the mucins which form hydrogen bonds with complimentary units on neighbouring mucins. Especially useful are charged mucoactive agents which, in addition to shielding some of the fixed charges along the macromolecular core of the mucin polymer also competing for the hydrogen bonding sites. This dual effect makes the mucus less stiff and reduces the number of entanglement cross-links with neighbouring macromolecules within the mucus, thereby reducing viscoelasticity due to ionic interactions. In one embodiment, the mucoactive agent having this dual effect is not dextran.

In a particularly preferred embodiment of the present invention, the mucoactive agent for reducing cross-linking is a glycosaminoglycan. Glycosaminoglycans are a group of heteropolysaccharides which contain an N-acetylated hexosamine in a characteristic repeating disaccharide unit. Heparin is a preferred glycosarinoglycan.

In one embodiment of the present invention, the heparin used in the compositions comprises UFH, i.e. high molecular weight heparin. Surprisingly, it has been discovered that this high molecular weight form of heparin is effective in assisting mucus clearance and it has even been found to be more effective than low molecular weight fractions in reducing human mucus viscoelasticity in vitro.

In an alternative embodiment, the heparin used as a mucoactive agent in the compositions of the present invention is low molecular weight fractions of heparin.

Further, analogues of heparin are commercially available and may also be used as mucoactive agents in the present invention. Such analogues include sulphated heparin and glycosylated heparin. Surprisingly, the inventors have found that sulphated heparin is more effective that non-sulphated heparin in reducing the elasticity of human mucus. Accordingly, in a preferred embodiment of the present invention, the composition comprises sulphated heparin as a mucoactive agent.

Heparin derivatives are commonly termed heparinoids and these may also be used in the compositions of the present invention. Heparinoids are closely related to heparin and share many of its properties. Heparinoids are useful for reducing cross-linking in mucus and they also exhibit anti-inflammatory properties.

Chondroitins are another group of glycosaminoglycans which may be used in the present invention, and these include dermatan sulphate and chondroitin sulphates. Keratin sulphate and hyaluronic acid are further glycosaminoglycans which may be used as mucoactive agents in the compositions of the present invention, as are heparitin sulphates such as heparan sulphate proteoglycan.

In one embodiment of the present invention, the mucoactive agent is danaparoid sodium. This low molecular weight heparinoid contains a mixture of the sodium salts of heparan sulphate, dermatan sulphate and chondroitin sulphate and is useful in reducing the cross-linking in mucus. Another heparinoid which may be used comprises a combination of heparin, dermatan sulphate and chondroitin sulphate.

Naturally occurring and synthetic highly sulphated glucosaminoglycans are also examples of mucoactive agents which may be included in the compositions of the present invention. These compounds, which are also known as glycosaminoglycan polysulphate compounds, or sulfated mucopolysaccharides are also useful in reducing cross-linking within the mucus to be cleared.

Other polysaccharides aside from glycosaminoglycans may be used as mucoactive agents which reduce cross-linking within mucus, such as dextrans. Preferably, the polysaccharide mucoactive agent should have a relatively low molecular weight. For instance, the agent should have an average molecular weight of less than 30,000, more preferably less than 20,000 and even more preferably less than 10,000.

Finally, a further group of mucoactive agents capable of assisting mucus clearance are amino acids. Particularly effective amino acids include basic amino acids such as lysine, arginine and histidine, and their derivatives. These amino acids are thought to assist mucus clearance by increasing the transepithelial potential difference, causing a stimulation of chlorine transport, which induces water movement into the epithelial lining fluid and further enhances the fluidification of the mucus. Other amino acids, such as cysteine, are thought to disrupt the di-sulphide bonds in the mucus. Amino acids, including hydrophobic amino acids such as leucine, also reduce cross-linking within the mucus.

Acetylcysteine (NAC) and the acetylcysteine salt derivative Nacystelyn (or NAL) are also effective mucoactive agents which are suitable for inclusion in the compositions of the present invention. Indeed, the efficacy of NAL is indicated in the experimental data discussed below.

In a further preferred embodiment, a charged agent is used to reduce cross-linking by shielding the charges on the mucins, thereby reducing the ionic interactions between adjacent mucins. Suitable charged agents include charged glycosaminoglycans, as discussed above, including, for example, heparin sulphate, heparan sulphates, or danaparoid sodiurm. Other polysaccharide sulphates or phosphates may also be used, such as dextran sulphates or phosphates. An alternative mucoactive agent capable of reducing cross-linking by shielding the charges on mucins is a sodium chloride solution or the like.

Suitable mucoactive agents for disrupting the cross-linking within the mucus by disrupting the di-sulphide bridges between glycoprotein subunits are compounds bearing free sulphydryl groups such as cysteine. These agents include the cysteine derivative NAC, the acetylcysteine salt derivative NAL and dithiothreitol.

In another embodiment of the present invention, preferably where the composition comprises just one mucoactive agent or where the composition does not include an additional active agent, the mucoactive agent is not dextran or a charged dextran, such as dextran sulphate or dextran phosphate. In another embodiment, the agent for reducing cross-linking is a dextran having a molecular weight of more than 5,000.

In yet another embodiment of the present invention, preferably where the composition comprises just one mucoactive agent or where the composition does not include an additional active agent, the mucoactive agent is not heparin or heparin sulphate, or is not low molecular weight heparin.

In another embodiment, preferably where the composition comprises just one mucoactive agent or where the composition does not include an additional active agent, the mucoactive agent is not rhDNase or is not NAC.

Various mucoactive agents assist mucus clearance by increasing the water content of the mucus. Some of these agents act by drawing additional water into the mucus, and are often referred to as osmolar agents or even non-destructive mucolytics. Alternatively, these agents work by blocking the uptake of salt and water across airway epithelium.

Suitable mucoactives for inclusion in the compositions of the present invention which act by drawing water into the mucus include low molecular weight sugars such as dextrans, dextrin, mannitol, glucose or urea. Various other monosaccharides, disaccharides and oligosaccharides also have an osmolytic effect. Amiloride is an agent which is supposed to block the uptake of salt and water across airway epithelium, thereby increasing hydration and diluting the macromolecular components of the mucus. Some of the derivatives of amiloride have a similar activity, including phenamil and benzamil.

Examples of mucoactive agents which are capable of assisting mucus clearance by digesting naked DNA and cell debris within the mucus include rhDNase, which digests the naked DNA. Filamentous actin may be degraded by depolymerising agents such as gelsolin and thymosin β4.

Mucoactive agents which reduce inflammation include the glycosarinoglycans discussed above, and in particular heparin, the heparinoids and the chondroitins. The use of such mucoactive agents allows the compositions of the present invention to simultaneously attack the excess mucus in the airways, but also to alleviate one of the particularly unpleasant results of that excess mucus, namely inflammation, which often results from the infection which is effectively encouraged by the excess mucus, as discussed above.

As will be clear from the foregoing discussion of mucoactive agents suitable for use in the present invention, many of these agents actually exhibit two or more of the desired effects on the mucus. For example, heparin reduces the cross-linking within the mucus and it has an anti-inflammatory effect. Dextrans may disrupt cross-linking in the mucus as well as triggering dilution of the mucus.

It should be noted that the heparin products such as unfractionated heparin include both high and low molecular weight heparin in a single product. These different forms of heparin may, as discussed above, have different effects on the mucus, so that combinations of hydrogen bond breaking, ionic interference and osmotic effect are observed from administration of this single product.

In one embodiment of the invention, the composition comprises a glycosaminoglycan and preferably a charged glycosaminoglycan.

In another embodiment of the present invention, the composition comprises at least two mucoactive agents. In one embodiment, at least one of the mucoactive agents is a glycosaminoglycan. In another embodiment, the two or more mucoactive agents have different effects on the mucus to one another, as discussed above.

The combination of different types of effects on the mucus, by virtue of the different mechanisms of assisting mucus clearance discussed above, is surprisingly effective. The combined effects are thought to reduce the viscosity and elasticity of the mucus, enabling clearance of the mucus from the lungs both through coughing and through ciliary movement.

What is more, some combinations of mucoactive agents exhibit a synergistic effect. For example, rhDNase has in the past been found to have limited effect on some patients and this was thought to be a result of the rhDNase having difficulty penetrating the mucus. However, when the rhDNase is co-administered with another mucoactive agent which is capable of disrupting the cross-links within the mucus, for example heparin, the rhDNase is better able to penetrate the gel structure and is therefore more effective. Thus, the effect of the combination of mucoactive agents is greater than the sum of the effects of the agents when they are administered individually.

In a preferred embodiment of the invention, the composition includes a combination of an agent for reducing cross-linking and an agent for diluting the mucus. For example, the agent for reducing cross-linking may be heparin or hepatin sulphate, cysteine, NAC or NAL, while the agent for diluting the mucus may be a low molecular weight sugar such as dextran. Another combination comprises a mixture of different heparins or heparinoids. Alternatively, the combination may comprise an agent for reducing cross-linking, such as a glycosaminoglycan, plus dextran, mannitol and/or lactose, in order to enhance the osmotic or hydrogen bond breaking effect. In another embodiment, the composition comprises an agent for reducing cross-linking, such as heparin, a heparinoid or other glycosaminoglycan and an amino acid such as lysine, cysteine or leucine. Another combination comprises heparin, dermatan sulphate and chondritin sulphate.

In another embodiment of the invention, the mucoactive agents are administered, either simultaneously or sequentially, with an antibiotic. For example, for treating CF, the antibiotic might be selected from tobramycin, gentamycin, ciprofloxin or colomycin. For treating COPD, the antibiotic might be amoxycillin, cotrimixazole or doxycycline. One or more antibiotics may be included in the composition with the one or more mucoactive agents.

In yet another embodiment of the invention, the mucoactive agents are administered, either simultaneously or sequentially, with an anti-inflammatory agent. For example, the anti-inflammatory agent might be selected from diclofenac sodium, ketoprofen, ibuprofen, nedocromil and cromoglycate. One or more anti-inflammatory agents may be included in the composition with the one or more mucoactive agents.

In yet another embodiment of the invention, the mucoactive agents are administered, either simultaneously or sequentially, with a surfactant. Surfactants are known to reduce adherence of mucus and help it to be cleared or may aid the spreading of the mucoactive composition once it is in the lungs. Surfactants, such as lecithin, natural or synthetic lung surfactants, or phospholipids such as DPPC, DPPE and other such lipids as known in the art, may advantageously affect the surface tension of the mucus and therefore assist its clearance.

Alternatively, the combinations may be one or more mucoactive agents with any one or more active agents selected from:

1) steroid drugs such as, for example, alcometasone, beclotnethasone, beclomethasone diptopionate, betamethasone, budesonide, clobetasol, deflazacort, diflucottolone, desoxymethasone, dexamethasone, fludrocortisone, flunisolide, fluocinolone, fluometholone, fluticasone, fluticasone proprionate, hydrocortisone, triamcinolone, nandtolone decanoate, neomycin sulphate, rimexolone, methylprednisolone and prednisolone;
2) antibiotic and antibacterial agents such as, for example, metronidazole, sulphadiazine, triclosan, neomycin, amoxicillin, amphotericin, clindamycin, aclarubicin, dactinomycin, nystatin, mupirocin and chlorhexidine;
3) antihistamines such as, for example, azelastine, chlorpheniramine, astemizole, cetirizine, cinnarizine, desloratadine, loratadine, hydroxyzine, diphenhydramine, fexofenadine, ketotifen, promethazine, trimeprazine and terfenadine;
5) anti-inflammatory agents such as, for example, piroxicam, nedocromil, benzydamine, diclofenac sodium, ketoprofen, ibuprofen, nedocromil, cromoglycate, fasafungine and iodoxamide;
6) anticholinergic agents such as, for example, atropine, benzatropine, biperiden, cyclopentolate, oxybutinin, orphenadine hydrochloride, glycopyrronium, glycopyrrolate, procyclidine, propantheline, propiverine, tiotropium, tropicamide, trospium, iprattopium bromide and oxittoprium bromide;
7) bronchodilators, such as salbutamol, fenoterol, formoterol and salmeterol;
8) sympathomimetic drugs, such as adrenaline, noradrenaline, dexamfetamine, dipirefin, dobutamine, dopexamine, phenylephrine, isoprenaline, dopamine, pseudoephedrine, tramazoline and xylometazoline;
9) anti-fungal drugs such as, for example, amphotericin, caspofungin, clotrimazole, econazole nitrate, fluconazole, ketoconazole, nystatin, itraconazole, terbinafine, voriconazole and miconazole;
10) local anaesthetics such as, for example, amethocaine, bupivacaine, hydrocortisone, methylprednisolone, prilocaine, proxymetacaine, ropivacaine, tyrothricin, benzocaine and lignocaine;
11) pharmaceutically acceptable salts of any of the foregoing.

The doses of mucoactive agents requited to have the desired effect of assisting mucus clearance will clearly depend upon the agents used. In general, the dose may comprise not more than 250 mg of one or more mucoactive agents, preferably not more than 200 mg, preferably not more than 150 mg, preferably not more than 100 mg, not more than 50 mg or not more than 20 mg. In the case of glycosaminoglycans such as heparin and heparinoids, the preferred delivered dose tends to be high, as large amounts of these agents are required for the desired effect on the mucus. The daily dose required is likely to be in the order of 100 to 200 mg per day and so individual doses of these mucoactive agents should be in the region of 20-120 mg, preferably 40-80 mg or 50-60 mg. Other mucoactive agents, such as NAC and NAL may be effective at lower concentrations and may therefore be used at lower doses or may be administered less frequently.

These are relatively large doses, even at the lower ends of the ranges and this presents some delivery problems which are addressed below.

The compositions of the present invention are well suited to the treatment of pulmonary and other diseases, whilst overcoming the problems associated with current treatments of such diseases. Preferably, the compositions would be used for treating diseases which have as a symptom the excess formation of mucus secretions in the airways, including chronic bronchitis, acute asthma, cystic fibrosis (CF), chronic obstructive pulmonary disease (COPD), bronchiectasis, hypersecretion resulting from epithelial damage such as allergic stimuli or mechanical abrasions, and nasal hypersecretion.

In a particularly preferred embodiment of the first aspect of the invention, the composition for assisting mucus clearance is in the form of a dry powder.

Preferably, the size of the powder particles is selected for deposition within the lung where the active agents will have a local effect. In particular, particles with an MMAD of less than 10 µm, less than 8 µm, less than 7 µm, less than 5 µm, less than 3 µm or less than 2 µm are preferred.

There is a general prejudice in this technical field against treating the excess mucus in the lungs of a patient suffering from CF, COPD or the like with a dry powder formulation. Such conditions have, in the past, almost exclusively been treated with solutions. Despite this prejudice, it has been found that formulating the compositions comprising one or more mucoactive agents as a dry powder is linked with a number of significant advantages which enable the present invention to be put into practice and put into practice in a commercially attractive manner.

When solutions or suspensions are to be administered to the lung by inhalation, this is done using nebulizers. These devices dispense solutions and suspensions in the form of a fine spray, and they typically have a face mask attached, so that the subject may inhale the fine spray through the mouth or nose. However, nebulizers tend to be large devices and they are generally not portable, frequently because they are pressurised by an oxygen tank. For this reason, nebulizers tend to be used to dispense medicaments to immobile patients and they are often unsuitable where an easy and convenient (self-) administration of a medicament is desired, as in the case with the present invention.

A further problem associated with the use of nebulizers is the difficulty obtaining accurate information regarding the dose actually delivered to the patient. There is also a general lack of precision, reproducibility and efficiency in the delivery of the medicament, leading to the need to increase the dose administered to ensure that the desired therapeutic effect is achieved, which results in drug wastage and an increased risk of adverse effects.

Finally, where relatively large doses of an active agent are to be administered to a patient, this often requires inhalation of the fine spray over an extended period of time. For example, in one study of the effect of inhaled heparin, a relatively small dose of 8,000 IU of heparin had to be administered over a period of 15 minutes. This is clearly not a convenient mode of administration.

In contrast, the devices used to deliver dry powder formulations are simple and relatively cheap, so that they can even be disposable. Furthermore, the devices are small and therefore easily portable. They are also very easy for a patient to use.

However, there are problems associated with formulating the compositions of the present invention as a dry powder. Firstly, due to their polyanionic nature, glycosaminoglycans are "sticky" molecules and they have been found to readily form aggregates when provided in particulate formation. Such aggregates are too large to teach the deep lung upon inhalation. Secondly, in order to assist in the clearance of mucus from the airways, a large dose of mucoactive agent is required. In order to be able to administer a dose of the order of 10's of milligrams of active agent by dry powder inhalation, a high dosing efficiency is required otherwise an unacceptable amount of powder would have to be inhaled into the lungs. Dry powder inhalers which are currently commercially available tend to have relatively poor dosing efficiency. With many of these dry powder formulations, it has been found that frequently only a small amount (often only about 10%) of the active particles that leave the device on inhalation are deposited in the lower lung. This is totally unacceptable where a large dose needs to be administered.

The present invention provides methods and compositions which enable the mucoactive agents to be efficiently dispensed as dry powders. These aspects of the invention are discussed in greater detail below.

Formulating dry powder formulations for use in the present invention presents problems, especially where the composition includes a "sticky" glycosaminoglycan such as heparin or heparinoids. The nature of these compounds mean that they do not lend themselves well to formulation in fine particulate form. Therefore, it is necessary to employ special formulating techniques in order to produce a powder which can be dispensed in an efficient manner so that it can assist mucus clearance. If a simple dry powder formulation is used, the dosing efficiency will be such that it will be all but impossible to administer enough of the mucoactive agent or agents to the lungs to have the desired effect of assisting mucus clearance.

The dosing efficiency is highly dependent on the fine particle fraction (FPF) of the dry powder formulation and various excipients need to be added in order to ensure that a high enough FPF is achieved.

A further obstacle to being able to deliver the composition of the present invention as a dry powder is the high dose of the mucoactive agents required in order to have an effect. The only way that a high enough dose can be administered without exposing the lungs to too much dry powder is for the dosing efficiency to be high. The usual maximum dose of drug delivered using a dry powder is in the order of 5 mg. In the present invention, the doses will frequently far exceed that level and, unless the dosing efficiency is very high, it will simply not be possible to deliver the large doses of mucoactive agent required.

Thus, the present invention is not merely the decision to use certain mucoactive agents or combinations of these agents. Rather, there is a significant amount of work required to put the invention into practice in such a way that it could be a pharmaceutical product.

The composition according to the present invention may be dispensed using any device which is suitable for pulmonary administration of a dry powder. Preferably, the composition is suitable for administration using a dry powder inhaler (DPI).

The compositions of the present invention may also include other substances, such as stabilisers or excipient materials. The particles of mucoactive agent will usually comprise at least 1% mucoactive agent, at least 50%, at least 75%, at least 90%, at least 95%, or at least 99% mucoactive agent. The particles of mucoactive agent may also include other substances such as stabilisers or excipient materials.

Other particles or materials included in the composition are intended to assist the efficient and reproducible delivery of the active particles from the delivery device to the lower respiratory tract or deep lung and these will be discussed in detail below.

The delivery of dry powder pharmaceutical compositions to the respiratory tract is known to present certain problems. The inhaler device (usually a DPI) should deliver the maximum possible proportion of the active particles expelled to the lungs, including a significant proportion to the lower lung, preferably at the low inhalation capabilities to which some patients are limited. As a result, much work has been done on improving dry powder formulations to increase the proportion of the active particles which is delivered to the lower respiratory tract or deep lung.

The type of dry powder inhaler used will affect the efficiency of delivery of the active particles to the respiratory tract. Also, the physical properties of the powder affect both the efficiency and reproducibility of delivery of the active particles and the site of deposition in the respiratory tract.

On exit from the inhaler device, the active particles should form a physically and chemically stable aerocolloid which remains in suspension until it reaches a conducting bronchiole or smaller branching of the pulmonary tree or other absorption site, preferably in the lower lung. Preferably, no active particles are exhaled from the absorption site.

When delivering a formulation to the lung for local action, the size of the active particles within the formulation is very important in determining the site of the absorption in the body.

For formulations to reach the deep lung via inhalation, the active agent in the formulation must be in the form of particles (active particles) that are very fine, for example having a mass median aerodynamic diameter (MMAD) of less than 10 µm. It is well established that particles having an MMAD of greater than 10 µm are likely to impact on the walls of the throat and generally do not reach the lung. Particles having an MMAD of 5 to 2 µm will generally be deposited in the respiratory bronchioles whereas particles having an MMAD of 3 to 0.05 µm are likely to be deposited in the alveoli and to be absorbed into the bloodstream.

As the mucoactive agents are to act directly on the mucus in the airways, the dry powder composition should be formulated for delivery to the lower respiratory tract. Thus, the dry powder formulation should preferably comprise particles of the mucoactive agent which have an MMAD of less than 10 µm or of approximately 2-5 µm. Preferably, at least 90% by weight of the mucoactive particles have a diameter within this range.

Due to the polyanionic nature of glycosaminoglycans, they readily form aggregates when provided in particulate formation. Such aggregates are too large to reach the deep lung. The inventors have, however, been able to provide particulate formulations comprising mucoactive agents such as glycosaminoglycans which are capable of being aerosolised in a dry powder inhaler and delivered to the deep lung.

Advantageously, the compositions of the present invention comprise at least 30%, at least 50%, at least 75%, at least 90%, at least 95% or at least 99% by weight of mucoactive agent based on the total weight of the formulation.

In addition to the "sticky" nature of mucoactive agents, the fine particles are also thermodynamically unstable due to their high surface area to volume ratio, which provides a significant excess surface free energy and encourages particles to agglomerate. In the inhaler, agglomeration of small particles and adherence of such particles to the walls of the inhaler are problems that result in the fine particles leaving the inhaler as large, stable agglomerates, or being unable to leave the inhaler and remaining adhered to the interior of the inhaler or even clogging or blocking the inhaler.

The uncertainty as to the extent of formation of stable agglomerates of the particles between each actuation of the inhaler and also between different inhalers and different batches of particles, leads to poor dose reproducibility. Furthermore, the formation of agglomerates means that the MMAD of the active particles can be vastly increased, so that the agglomerates of the active particles do not teach the desired part of the lung for the required therapeutic effect.

According to a preferred embodiment, the compositions of the present invention firstly provide a high fine particle fraction (FPF) and fine particle dose (FPD) upon aerosolisation of the formulation. Additionally, the compositions comprise particles of the correct MMAD to be deposited in the correct part of the lung. Advantageously, the present invention has identified a number of simple methods of preparing these compositions having good FPFs and FPDs and accurate particle size range.

The metered dose (MD) of a dry powder formulation is the total mass of active agent present in the metered form presented by the inhaler device in question. For example, the MD might be the mass of active agent present in a capsule for a Cyclohaler (trademark), or in a foil blister in an Aspirair (trademark) device.

The emitted dose (ED) is the total mass of the active agent emitted from the device following actuation. It does not include the material left on the internal or external surfaces of the device, or in the metering system including, for example, the capsule or blister. The ED is measured by collecting the total emitted mass from the device in an apparatus frequently identified as a dose uniformity sampling apparatus (DUSA), and recovering this by a validated quantitative wet chemical assay.

The fine particle dose (FPD) is the total mass of active agent which is emitted from the device following actuation which is present in an aerodynamic particle size smaller than a defined limit. This limit is generally taken to be 5 µm if not expressly stated to be an alternative limit, such as 3 µm or 2 µm, etc. The FPD is measured using an impactor or impinger, such as a twin stage impinger (TSI), multi-stage liquid impinger (MSLI), Andersen Cascade Impactor (ACI) or a Next Generation Impactor (NGI). Each impactor or impinger has a pre-determined aerodynamic particle size collection cut points for each stage. The FPD value is obtained by interpretation of the stage-by-stage active agent recovery quantified by a validated quantitative wet chemical assay where either a simple stage cut is used to determine FPD or a more complex mathematical interpolation of the stage-by-stage deposition is used.

The fine particle fraction (FPF) is normally defined as the FPD divided by the ED and expressed as a percentage. Herein, the FPF of ED is referred to as FPF(ED) and is calculated as FPF(ED)=(FPD/ED)×100%.

The fine particle fraction (FPF) may also be defined as the FPD divided by the MD and expressed as a percentage. Herein, the FPF of MD is referred to as FPF(MD), and is calculated as FPF(MD)=(FPD/MD)×100%.

The tendency of fine particles to agglomerate means that the FPF of a given dose is highly unpredictable and a variable proportion of the fine particles will be administered to the lung, or to the correct part of the lung, as a result.

In an attempt to improve this situation and to provide a consistent FPF and FPD, dry powder formulations often include additive material.

The additive material is intended to decrease the cohesion between particles in the dry powder formulation. It is thought that the additive material interferes with the weak bonding forces between the small particles, helping to keep the particles separated and reducing the adhesion of such particles to one another, to other particles in the formulation if present and to the internal surfaces of the inhaler device. Where agglomerates of particles are formed, the addition of particles of additive material decreases the stability of those agglomerates so that they are more likely to break up in the turbulent air stream created on actuation of the inhaler device, whereupon the particles are expelled from the device and inhaled. As the agglomerates break up, the active particles return to the form of small individual particles which are capable of reaching the lower lung.

In the prior art, dry powder formulations are discussed which include distinct particles of additive material (generally of a size comparable to that of the fine active particles). In some embodiments, the additive material may form either a continuous or a discontinuous coating on the active particles and/or any carrier particles.

Preferably, the additive material is an anti-adherent material and it will tend to reduce the cohesion between particles and will also prevent fine particles becoming attached to the inner surfaces of the inhaler device. Advantageously, the additive material is an anti-friction agent or glidant and will give better flow of the pharmaceutical composition in the inhaler. The additive materials used in this way may not necessarily be usually referred to as anti-adherents or anti-friction agents, but they will have the effect of decreasing the cohesion between the particles or improving the flow of the powder. The additive materials are often referred to as force control agents (FCAs) and they usually lead to better dose reproducibility and higher fine particle fractions.

Therefore, an FCA, as used herein, is an agent whose presence on the surface of a particle can modify the adhesive and cohesive surface forces experienced by that particle, in the presence of other particles. In general, its function is to reduce both the adhesive and cohesive forces.

In general, the optimum amount of additive material to be included in a dry powder formulation will depend on the chemical composition and other properties of the additive material and of the active material, as well as upon the nature of other particles such as carrier particles, if present. In general, the efficacy of the additive material is measured in terms of the fine particle fraction of the composition.

Known additive materials usually consist of physiologically acceptable material, although the additive material may not always reach the lung. For example, where the additive particles are attached to the surface of carrier particles, they will generally be deposited, along with those carrier particles, at the back of the throat of the user.

In a further attempt to reduce agglomeration of the fine active particles and to provide a consistent FPF and FPD, dry powder formulations often include coarse carrier particles of excipient material mixed with the fine particles of active material. Rather that sticking to one another, the fine active particles tend to adhere to the surfaces of the coarse carrier particles whilst in the inhaler device, but are supposed to release and become dispersed upon actuation of the dispensing device and inhalation into the respiratory tract, to give a fine suspension. The carrier particles preferably have MMADs greater than 60 µm.

The inclusion of coarse carrier particles is attractive where relatively small doses of active agent are dispensed. It is very difficult to accurately and reproducibly dispense very small quantities of powder and small variations in the amount of powder dispensed will mean large variations in the dose of active agent where the powder comprises mainly active particles. Therefore, the addition of a diluent, in the form of large excipient particles will make dosing more reproducible and accurate. However, the doses of mucoactive agents such as heparin required to have an effect on mucus clearance are relatively large. This means that the inclusion of carrier particles in some of the compositions according to the invention to enhance the FPF and FPD values is unattractive or simply not an option.

If included in the compositions of the present invention, carrier particles may be of any acceptable excipient material or combination of materials. For example, the carrier particles may be composed of one or more materials selected from sugar alcohols, polyols and crystalline sugars. Other suitable carriers include inorganic salts such as sodium chloride and calcium carbonate, organic salts such as sodium lactate and other organic compounds such as polysaccharides and oligosaccharides. Advantageously, the carrier particles are composed of a polyol. In particular, the carrier particles may be particles of crystalline sugar, for example mannitol, dextrose or lactose. Preferably, the carrier particles are composed of lactose or mannitol, which is a mucoactive agent, as discussed above.

Advantageously, substantially all (by weight) of the carrier particles have a diameter which lies between 20 μm and 1000 μm, more preferably 50 μm and 1000 μm. Preferably, the diameter of substantially all (by weight) of the carrier particles is less than 355 μm and lies between 20 μm and 250 μm.

Preferably, at least 90% by weight of the carrier particles have a diameter between from 40 μm to 180 μm. The relatively large diameter of the carrier particles improves the opportunity for other, smaller particles to become attached to the surfaces of the carrier particles and to provide good flow and entrainment characteristics, as well as improved release of the active particles in the airways to increase deposition of the active particles in the lower lung.

The ratios in which the carrier particles (if present) and composite active particles are mixed will, of course, depend on the type of inhaler device used, the type of active particles used and the required dose. The carrier particles may be present in an amount of at least 50%, more preferably 70%, advantageously 90% and most preferably 95% based on the combined weight of the composite active particles and the carrier particles.

However, a further difficulty is encountered when adding coarse carrier particles to a composition of fine active particles and that difficulty is ensuring that the fine particles detach from the surface of the large particles upon actuation of the delivery device.

The step of dispersing the active particles from other active particles and from carrier particles, if present, to form an aerosol of fine active particles for inhalation is significant in determining the proportion of the dose of active material which reaches the desired site of absorption in the lungs. In order to improve the efficiency of that dispersal it is known to include in the composition additive materials, including FCAs of the nature discussed above. Compositions comprising fine active particles and additive materials are disclosed in WO 97/03649 and WO 96/23485.

In light of the foregoing problems associated with known dry powder formulations, even when they include additive material and/or carrier particles, it is an aim of the present invention to provide dry powder compositions which have physical and chemical properties which lead to an enhanced FPF and FPD. This will lead to greater dosing efficiency, with a greater proportion of the dispensed active agent reaching the desired part of the lung for achieving the required therapeutic effect.

In particular, the present invention seeks to optimise the preparation of particles of active agent used in the dry powder composition by engineering the particles making up the dry powder composition and, in particular, by engineering the particles of active agent. Furthermore, cohesion between particles is to be reduced in order to enhance the FPF and FPD of the dry powder compositions. This is done by preparing the heparin particles in the presence of an FCA.

Whilst the FPF and FPD of a dry powder formulation are dependent on the nature of the powder itself, these values are also influenced by the type of inhaler used to dispense the powder. Dry powder inhalers can be "passive" devices in which the patient's breath is the only source of gas which provides a motive force in the device. Examples of "passive" dry powder inhaler devices include the Rotahaler and Diskhaler (GlaxoSmithline) and the Turbohaler (Astra-Draco) and Novolizer (trade mark) (Viatris GmbH). Alternatively, "active" devices may be used, in which a source of compressed gas or alternative energy source is used. Examples of suitable active devices include Aspirair (trade mark) (Vectura Ltd—see WO 01/00262 and GB2353222) and the active inhaler device produced by Nektar Therapeutics (as covered by U.S. Pat. No. 6,257,233). As a rule, the FPF obtained using a passive device will tend not to be as good as that obtained with the same powder but using an active device.

In one embodiment of the invention, the dry powder composition has an FPF of at least 40%, and preferably has an FPF of at least 50%. The FPF(ED) may be between 50 and 99%, more preferably between 70 and 99% and most preferably between 80 and 99%. The FPF(MD) may be at least 35%. Preferably, the FPF(MD) will be between 40 and 99%, more preferably between 50 and 95% and most preferably between 70 and 90%.

In a yet another embodiment, the pharmaceutical composition comprises at least one mucoactive agent and a force control agent, the force control agent preferably being present on the surface of particles of mucoactive agent. In a further embodiment, the pharmaceutical composition comprises at least one mucoactive agent in combination with an active agent selected from the list above and a force control agent, the force control agent preferably being present on the surface of particles of mucoactive agent.

The preferred FCAs to be included in the compositions of the invention may be any of the additive materials discussed above. Preferably, the FCA is selected from amino acids, and especially hydrophobic amino acids, peptides and polypeptides having a molecular weight of between 0.25 and 1000 kDa and derivatives thereof, dipolar ions such as zwitterions, phospholipids such as lecithin, and metal stearates such as magnesium stearate. Particularly preferred are amino acids and especially leucine, lysine and cysteine.

Known FCAs usually consist of physiologically acceptable material, although the FCA may not always reach the lung. For example, where the FCA particles are attached to the surface of carrier particles, they will generally be deposited, along with those carrier particles, at the back of the throat of the user.

The FCAs used in the present invention may be film-forming agents, fatty acids and their derivatives, lipids and lipid-like materials, and surfactants, especially solid surfactants.

Advantageously, the FCA includes one or more compounds selected from amino acids and derivatives thereof, and peptides and derivatives thereof. Amino acids, peptides and derivatives of peptides are physiologically acceptable and give acceptable release of the active particles on inhalation.

It is particularly advantageous for the FCA to comprise an amino acid. The FCA may comprise one or more of any of the following amino acids: leucine, isoleucine, lysine, cysteine, valine, methionine, and phenylalanine. The FCA may be a salt or a derivative of an amino acid, for example aspartame, acesulfame K, or acetyl cysteine. Preferably, the FCA consists substantially of an amino acid, more preferably of leucine, advantageously L-leucine. The D- and DL-forms may also be used. As indicated above, L-leucine has been found to give particularly efficient dispersal of the active particles on inhalation. Lysine and cysteine are also useful as FCAs. As discussed above, these amino acids are also mucoactive agents. In another embodiment, the amino acid is not glycine or alanine.

The FCA may include one or more water soluble substances. This helps absorption of the substance by the body if the FCA reaches the lower lung. The FCA may include dipolar ions, which may be zwitterions.

Alternatively, the FCA may comprise a phospholipid or a derivative thereof. Lecithin has been found to be a good material for use as an FCA.

The FCA may comprise a metal stearate, or a derivative thereof, for example, sodium stearyl fumarate or sodium stearyl lactylate. Advantageously, the FCA comprises a metal stearate. For example, zinc stearate, magnesium stearate, calcium stearate, sodium stearate or lithium stearate. Preferably, the FCA comprises magnesium stearate.

The FCA may include or consist of one or more surface active materials, in particular materials that are surface active in the solid state. These may be water soluble or able to form a suspension in water, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof, such as glyceryl behenate. Specific examples of such materials are: phosphatidylcholines, phosphatidylethanolamines, phosphatidylglycerols, phosphatidylinositol and other examples of natural and synthetic lung surfactants; lauric acid and its salts, for example, sodium lauryl sulphate, magnesium lauryl sulphate; triglycerides such as Dynsan 118 and Cutina HR; and sugar esters in general. Alternatively, the FCA may be cholesterol or natural cell membrane materials, including pollen or spore cell wall components such as sporo-pollenins.

Other possible FCAs include sodium benzoate, hydrogenated oils which are solid at room temperature, talc, titanium dioxide, aluminium dioxide, silicon dioxide and starch.

In embodiments, a plurality of different FCAs can be used.

According to a second aspect of the present invention, methods are provided for producing compositions according to the first aspect of the invention.

Spray drying is a well-known and widely used technique for producing particles of material. To briefly summarise, the material to be made into particles is dissolved or dispersed in a liquid or can be made into a liquid which is sprayed through a nozzle under pressure to produce a mist or stream of fine liquid droplets. These fine droplets are usually exposed to heat which rapidly evaporates the excess volatile liquid in the droplets, leaving effectively dry powder particles.

According to another aspect of the present invention, the compositions of the present invention are prepared by spray drying. In one embodiment, the spray drying process involves co-spray drying the one or more mucoactive agents with one or more force control agents.

The combination or blend of one or more mucoactive agents, optionally one or more other additional active agents, and FCA which is spray dried to form a dry powder formulation can be a solution or suspension in a host liquid. In some embodiments, all or at least a proportion of the mucoactive agent and/or FCA is or are in solution in the host liquid before being subjected to spray drying. Substantially all of the mucoactive agent and FCA can be in solution in the host liquid before being subjected to spray drying.

The one or more mucoactive agents are preferably at least 1.5, 2, 4 and, more preferably, at least 10 times more soluble than the FCA in the host liquid at the spraying temperature and pressure. In preferred embodiments, this relationship exists at a temperature between 30 and 60° C. and atmospheric pressure. In other embodiments, this relationship exists at a temperature between 20 to 30° C. and atmospheric pressure, or, preferably, at 20° C. and atmospheric pressure.

In addition to the above discussed spray drying technique, alternative techniques for producing fine particles may be used, such as spray freeze drying and freeze drying.

In another embodiment of the invention, the one or more mucoactive agents are spray dried using a non-conventional spray drier comprising a means for producing droplets moving at a controlled velocity and of a predetermined size. The advantages of this control of the droplet formation and drying profile will be discussed in greater detail below.

Finally, the spray drying process may also include a further step wherein the moisture content of the spray dried particles is adjusted, in order to "fine-tune" the properties of the particles. This is also discussed in greater detail below.

It has been discovered that the FPF and FPD of the dry powder formulation is affected by the means used to create the droplets which are spray dried. Different means of forming droplets can affect the size and size distribution of the droplets, as well as the velocity at which the droplets travel when formed and the gas flow around the droplets. In this regard, the velocity at which the droplets travel when formed and the gas (which is usually air) flow around the droplets can dramatically affect size, size distribution and shape of resulting dried particles.

A method of preparing a dry powder composition is provided, wherein the one or more mucoactive agents are spray dried using a spray drier comprising a means for producing droplets moving at a controlled velocity and of a predetermined droplet size. The velocity of the droplets is preferably controlled relative to the body of gas into which they are sprayed. This can be achieved by controlling the droplets' initial velocity and/or the velocity of the body of gas into which they are sprayed.

It is clearly desirable to be able to control the size of the droplet formed during the spray drying process and the droplet size will affect the size of the dried particle. Preferably, the droplet forming means also produces a relatively narrow droplet, and therefore particle, size distribution. This will lead to a dry powder formulation with a more uniform particle size and thus a more predictable and consistent FPF and FPD.

The ability to control the velocity of the droplet also allows further control over the properties of the resulting particles. In particular, the gas speed around the droplet will affect the speed with which the droplet dries. In the case of droplets which are moving quickly, such as those formed using a two-fluid nozzle arrangement (spraying into air), the air around the droplet is constantly being replaced. As the solvent evaporates from the droplet, the moisture enters the air around the droplet. If this moist air is constantly replaced by fresh, dry air, the rate of evaporation will be increased. In contrast, if the droplet is moving through the air slowly, the air around the droplet will not be replaced and the high humidity around the droplet will slow the rate of drying. As discussed below in greater detail, the rate at which a droplet dries affects various properties of the particles formed, including FPF and FPD.

Preferably the velocity of droplets at 10 mm from their point of generation is less than 100 m/s, more preferably less than 50 m/s and most preferably less than 20 m/s. Preferably the velocity of the gas, used in the generation of the droplets, at 10 mm from the point at which the droplets are generated is less than 100 m/s, more preferably less than 50 m/s and most preferably less than 20 m/s. In an embodiment, the velocity of the droplets relative to the body of gas into which they are sprayed, at 10 mm from their point of generation, is less than 100 m/s, more preferably less than 50 m/s and most preferably less than 20 m/s.

Preferably, the means for producing droplets moving at a controlled velocity and of a predetermined size is an alternative to the commonly used two-fluid nozzle. In one embodiment, an ultrasonic nebuliser (USN) is used to form the droplets in the spray drying process.

Whilst ultrasonic nebulisers (USNs) are known, these are conventionally used in inhaler devices, for the direct inhalation of solutions containing drug, and they have not previously been widely used in a pharmaceutical spray drying apparatus. It has been discovered that the use of such a nebuliser in a process for spray drying particles for inhalation has a number of important advantages and these have not previously been recognised. The preferred USNs control the velocity of the droplets and therefore the rate at which the particles are dried, which in turn affects the shape and density of the resultant particles. The use of USNs also provides an opportunity to perform spray drying on a larger scale than is possible using conventional spray drying apparatus with conventional types of nozzles used to create the droplets, such as two-fluid nozzles.

As USNs do not require a high gas velocity to generate the droplets, the dryer may provide greater control of the shape, velocity and direction of the plume than is possible with conventional two-fluid, pressure or rotary atomisers. Advantages therefore include reduced drier wall deposition, better controlled and more consistent drying rate. Reduced plume velocity means that smaller drying units are possible.

The preferable USNs use an ultrasonic transducer which is submerged in a liquid. The ultrasonic transducer (a piezoelectric crystal) vibrates at ultrasonic frequencies to produce the short wavelengths required for liquid atomisation. In one common form of USN, the base of the crystal is held such that the vibrations are transmitted from its surface to the nebuliser liquid, either directly or via a coupling liquid, which is usually water. When the ultrasonic vibrations are sufficiently intense, a fountain of liquid is formed at the surface of the liquid in the nebuliser chamber. Large droplets are emitted from the apex and a "fog" of small droplets is emitted. A schematic diagram showing how a standard USN works is shown in FIG. 1.

Preferably, the output per single piezo unit (for such a unit oscillating at >1.5 MegaHz) is greater than 1.0 cc/min, greater than 3.0 cc/min, greater than 5.0 cc/min, greater than 8.0 cc/min, greater than 10.0 cc/min, greater than 15.0 cc/min or greater than 20.0 cc/min. Such units should then produce dry particles with at least 90% by weight of the particles having a size of less than 3 μm, less than 2.5 μm or less than 2 μm, as measured by Malvern Mastersizer from a dry powder dispersion unit.

Preferably, the output per single piezo unit (for such a unit oscillating at >2.2 MegaHz) is greater than 0.5 cc/min, greater than 1.0 cc/min, greater than 3.0 cc/min, greater than 5.0 cc/min, greater than 8.0 cc/min, greater than 10.0 cc/min, greater than 15.0 cc/min or greater than 20.0 cc/min. Such units should then produce dry particles with d(90) of less than 3 μm, less than 2.5 μm, or less than 2 μm, as measured by Malvern Mastersizer from a dry powder dispersion unit.

The attractive characteristics of USNs for producing fine particle dry powders for inhalation include: low spray velocity; the small amount of carrier gas required to operate the nebulisers; the comparatively small droplet size and narrow droplet size distribution produced; the simple nature of the USNs (the absence of moving parts which can wear, contamination, etc.); the ability to accurately control the gas flow around the droplets, thereby controlling the rate of drying; and the high output rate which makes the production of dry powders using USNs commercially viable in a way that is difficult and expensive when using a conventional two-fluid nozzle arrangement. This is because scaling-up of conventional spray drying apparatus is difficult and the use of space is inefficient in conventional spray drying apparatus which means that large scale spray drying requires many apparatus and much floor space.

USNs do not separate the liquid into droplets by increasing the velocity of the liquid. Rather, the necessary energy is provided by the vibration caused by the ultrasonic nebuliser.

Furthermore, the USNs may be used to adjust the drying of the droplets and to control the expression of the force control agent on the surface of the resultant particles. Where the active agent itself can act as a force control agent, spray drying with a USN can further help to control the positioning of the hydrophobic moieties so that the effect of including a force control agent can be achieved even without including one.

Thus, as an alternative to the conventional Büchi two-fluid nozzle, an ultrasonic nebuliser may be used to generate droplets, which are then dried within the Büchi drying chamber. In one arrangement, the USN is placed in the feed solution comprising an active agent in a specially designed glass chamber which allows introduction of the cloud of droplets generated by the USN directly into the heated drying chamber of the spray dryer.

The two-fluid nozzle is left in place to seal the hole in which it normally sits, but the compressed air is not turned on. The drying chamber is then heated up to 150° C. inlet temperature, with 100% aspirator setting. Due to the negative pressure of the Büchi system, the nebulised cloud of droplets is easily drawn into the drying chamber, where the droplets are dried to form particles, which are subsequently classified by the cyclone, and collected in the collection jar. It is important that the level of feed solution in the chamber is regularly topped up to avoid over concentration of the feed solution as a result of continuous nebulisation.

When a spray drying process involves the use of a conventional nozzle for forming the droplets to be dried, such as a two-fluid nozzle, high gas flow speed rates around the droplets lead to a fast rate of drying. In comparison, because the gas speed around droplets formed using a USN is low in comparison, droplets formed using a USN dry more slowly than those produced by using conventional two-fluid nozzles. This has several marked effects on the particles produced.

Where the droplets dry quickly, a wrinkled particle morphology is observed, especially when the active agent is co-spray dried with an FCA. It is considered that the reduced rate of solvent evaporation from the droplets formed using a USN leads to reduced "blowing" which is the phenomenon which leads to the wrinkled particle morphology. Therefore, physically smaller and smoother primary particles that are observed when particles are produced using a USN.

It is also speculated that the slower drying rate which is expected when the droplets are formed using USNs allows the co-spray dried FCA to migrate to the surface of the droplet during the drying process. This migration may be further assisted by the presence of a (polar) solvent which encourages the hydrophobic moieties of the FCA to become positioned on the surface of the droplet. For example, an aqueous solvent is thought to be of assistance in this regard.

With the FCA being able migrate to the surface of the droplet so that it is present on the surface of the resultant particle, it is clear that a greater proportion of the FCA which is included in the droplet will actually have the force controlling effect (as the FCA must be present on the surface in order for it to have this effect). Therefore, it also follows that the use of USNs has the further advantage that it requires the addition of less FCA to produce the same force controlling effect in the resultant particles, compared to particles produced using conventional spray drying methods.

Naturally, where the active agent itself has hydrophobic moieties which can be presented as a dominant composition on the particle surface, excellent FPF and FPD values may be achieved with little or no separate FCA. Indeed, in such circumstances, the active agent itself acts as an FCA, because of the arrangement of its hydrophobic moieties on the surfaces of the particles.

It was previously thought that the wrinkled particle morphology was desirable as it was though that it helped to reduce particle adhesion and cohesion. It has also previously been speculated that this particle morphology may even help the particles to fly when they are expelled for the inhaler device. However, despite this speculation, the inventors actually feel that the chemical nature of the particle surfaces may be even more influential on the performance of the particles in terms of FPF, ED, etc. In particular, it is thought that the presence of hydrophobic moieties on the surface of particles is mote significant in reducing cohesion than the presence of craters or dimples. Therefore, contrary to the suggestion in the prior art, it is not necessary to seek to produce extremely dimpled or wrinkled particles in order to provide good FPF values.

Indeed, it is actually be advantageous not to produce severely dimpled or wrinkled particles, as these can yield low density powders, with very high voidage between particles. Such powders occupy a large volume relative to their mass as a consequence of this form, and can result in packaging problems, i.e., much larger blisters or capsules are required for a given mass of powder. High density powders, such as those produced using USNs in a spray drying process may, therefore, be of benefit, especially in the present invention where the dose of active agent to be administered is high.

What is more, as indicated above, the effect of the FCA included in the spray dried particles is magnified when the droplets are formed using alternative means, such as a USN, because of the migration of the additive to the particle surface. This in turn means that less FCA needs to be included and, where high doses of active agent are required, this is a further advantage.

Preferably, powders according to the present invention have a tapped density of at least 0.1 g/cc, at least 0.2 g/cc, at least 0.3 g/cc, at least 0.4 g/cc or at least 0.5 g/cc.

As discussed above, at least some of the mucoactive agents to be included in the compositions of the present invention are required in large quantities. It is therefore not desirable to include additional materials such as carriers or bulking agents in the compositions or in the particles. Thus, in one embodiment of the invention, the spray drying method of producing the particles for use in the compositions of the present invention does not involve co-spray drying the active agent with a carrier or bulking agent.

One would expect to get similar results to those shown above using USNs when using other means which produce low velocity droplets at high output rates. For example, further alternative nozzles may be used, such as electrospray nozzles or vibrating orifice nozzles. These nozzles, like the ultrasonic nozzles, are momentum free, resulting in a spray which can be easily directed by a carrier air stream. However, their output rate is generally lower than that of the USNs described above.

Another attractive type of nozzle for use in a spray drying process is one which utilises electro-hydrodynamic atomisation. A tailor cone is created, for example, at a fine needle by applying high voltage at the tip. This shatters the droplets into an acceptable monodispersion. This method does not use a gas flow, except to transport the droplets after drying. An acceptable monodispersion can also be obtained utilising a spinning disc generator.

The nozzles such as ultrasonic nozzles, electrospray nozzles or vibrating orifice nozzles can be arranged in a multi-nozzle array, in which many single nozzle orifices are arranged in a small area and facilitate a high total throughput of feed solution. The ultrasonic nozzle is an ultrasonic transducer (a piezoelectric crystal). If the ultrasonic transducer is located in an elongate vessel the output may be raised significantly.

When mucoactive particles are produced by spray drying, some moisture will remain in the particles. This is especially the case where the mucoactive agent is temperature sensitive and does not tolerate high temperatures for the extended period of time which would normally be required to remove further moisture from the particles.

The amount of moisture in the particles will affect various particle characteristics, such as density, porosity, flight characteristics, and the like.

Therefore, a method of preparing a dry powder composition is also provided, wherein the method comprises a step of adjusting the moisture content of the particles.

In one embodiment, the moisture adjustment or profiling step involves the removal of moisture. Such a secondary drying step preferably involves freeze-drying, wherein the additional moisture is removed by sublimation. An alternative type of drying is vacuum drying.

Generally, the secondary drying takes place after the active agent has been co-spray dried with an FCA. In another embodiment, the secondary drying takes place after nebulised mucoactive agent has been spray dried, wherein the active agent was optionally in a blend with a FCA.

The secondary drying step has two particular advantages. Firstly, it can be selected so as to avoid exposing the heparin to high temperatures for prolonged periods. Furthermore, removal of the residual moisture by secondary drying can be significantly cheaper than removing all of the moisture from the particle by spray drying. Thus, a combination of spray drying and freeze-drying or vacuum drying is economical and efficient, and is suitable for temperature sensitive pharmaceutically active agents.

Secondary drying significantly reduces the moisture content of mucoactive particles (from approximately 8.5% to 2%). This would imply that the mucoactive particles are drying in such a way that there is a hard outer shell holding residual moisture, which is driven off by secondary drying, and further moisture is trapped with in a central core. One could infer that the residence time of the particle in the drying chamber is too short, and that the outer shell is being formed rapidly and is too hard to permit moisture to readily escape during the initial spray drying process.

Secondary drying can also be beneficial to the stability of the product, by bringing down the moisture content of a powder. It also means that drugs which may be very heat sensitive can be spray dried at lower temperatures to protect them, and then subjected to secondary drying to reduce the moisture further and thereby to protect the drug.

In another embodiment of the third aspect of the invention, the moisture profiling involves increasing the moisture content of the spray dried particles.

Preferably, the moisture is added by exposing the particles to a humid atmosphere. The amount of moisture added can be controlled by varying the humidity and/or the length of time for which the particles are exposed to this humidity.

Following spray drying, which also optionally may include secondary drying, it may also be advantageous to mill the powders, for example in an air jet mill, in order to separate any particle agglomerates which have formed strong bridges between particles.

In a yet further embodiment of the present invention, instead of spray drying the one or more mucoactive agents to form a dry powder formulation, it is also possible to use other methods of preparing a dry powder. For example, many dry powders are formed by micronisation, that is, grinding up larger particles to form small particles of a desired size.

Techniques known as co-milling and mechanofusion, as described in detail in International Publication No. WO 02/43701, produce composite active particles and also are suitable for preparing the dry powder formulations of the present invention.

The composite active particles formed by co-milling and mechanofusion in the present invention are very fine particles of one or more mucoactive agents which have, upon their surfaces, an amount of an FCA. The FCA is preferably in the form of a coating on the surfaces of the particles of one or more mucoactive agents. The coating may be a discontinuous coating. The FCA may be in the form of particles adhering to the surfaces of the particles of one or more mucoactive agents. As explained below, at least some of the composite active particles may be in the form of agglomerates.

When the composite active particles are included in a pharmaceutical composition, the FCA promotes the dispersal of the composite active particles on administration of that composition to a patient, via actuation of an inhaler, as discussed above. Thus, once again, the presence of the FCA is able to increase the FPF and FPD of the dry powder formulation.

It has also been found that the milling of the particles of one or more mucoactive agents in the presence of an FCA produces significantly smaller particles and/or requires less time and less energy than the equivalent process carried out in the absence of the FCA. This allows composite active particles to be produced which have a mass median aerodynamic diameter (MMAD) or a volume median diameter (VMD) of less than 5, 4, 3 or 2 μm. It is often much easier to obtain small particles by this method than by other milling methods.

It is known that a milling process will tend to generate and increase the level of amorphous material on the surfaces of the milled particles thereby making them more cohesive. In contrast, the composite particles of the invention will often be found to be less cohesive after the milling treatment.

The word "milling" as used herein refers to any mechanical process which applies sufficient force to the particles of active material that it is capable of breaking coarse particles (for example, particles of mass medium aerodynamic diameter greater than 100 μm) down to fine particles of mass median aerodynamic diameter not more than 50 μm or which applies a relatively controlled compressive force as described below in relation to the mechanofusion, cyclomixing and similar methods.

A high degree of force is required to separate the individual particles of one or more mucoactive agents (which tend to agglomerate, especially if they include heparin which is sticky) such that effective mixing and effective application of the FCA to the surfaces of those particles is achieved. It is believed that an especially desirable aspect of the milling process is that the FCA may become deformed in the milling and may be smeared over or fused to the surfaces of the mucoactive particles. It should be understood, however, that in the case where the particles of one or more mucoactive agents are already fine, for example, having an MMAD below 20 μm prior to the milling step, the size of those particles may not be significantly reduced. The important thing is that the milling process applies a sufficiently high degree of force or energy to the particles.

The method generally involves bringing the particles of FCA into close contact with the surfaces of the mucoactive particles in order to achieve coated particles. A degree of intensive mixing is required to ensure a sufficient break-up of agglomerates of both constituents, dispersal and even distribution of FCA over the mucoactive particles.

As a consequence of the milling step, complete or partial, continuous or discontinuous, porous or non-porous coatings may be formed. The coatings originate from a combination of heparin and FCA particles. They are not coatings such as those formed by wet processes that require dissolution of one or both components. In general, such wet coating processes are likely to be more costly and more time consuming than the milling process of the invention and also suffer from the disadvantage that it is less easy to control the location and structure of the coating.

A wide range of milling devices and conditions are suitable for use in the method of the invention. The milling conditions, for example, intensity of milling and duration, should be selected to provide the required degree of force.

Ball milling is a suitable milling method. Centrifugal and planetary ball milling are especially preferred methods. Alternatively, a high pressure homogeniser may be used in which a fluid containing the particles is forced through a valve at high pressure producing conditions of high shear and turbulence.

Shear forces on the particles, impacts between the particles and machine surfaces or other particles and cavitation due to acceleration of the fluid may all contribute to the fracture of the particles and may also provide a compressive force.

Such homogenisers may be more suitable than ball mills for use in large scale preparations of the composite active particles.

Suitable homogenisers include EmulsiFlex high pressure homogenisers which are capable of pressures up to 4000 Bar, Niro Soavi high pressure homogenisers (capable of pressures up to 2000 Bar), and Microfluidics Microfluidisers (maximum pressure 2750 Bar). The milling step may, alternatively, involve a high energy media mill or an agitator bead mill, for example, the Netzch high energy media mill, or the DYNO-mill (Willy A. Bachofen AG, Switzerland). Alternatively, the milling may be a dry coating high energy process such as a MechanoFusion system (Hosokawa Micron Ltd), a Hybridizer (Nara) or any similar highly intense compressive process.

Other possible milling devices include air jet mills, pin mills, hammer mills, knife mills, ultracentrifugal mills and pestle and mortar mills.

Especially preferred methods are those involving the MechanoFusion, Hybridiser and Cyclomix instruments. Also especially preferred is an air jet mill.

Other suitable methods include ball and high energy media mills which are also capable of providing the desired high shear force and compressive stresses between surfaces, although as the clearance gap is not controlled, the coating process may be less well controlled than for mechanofusion milling and some problems such as a degree of undesired re-agglomeration may occur. These media mills may be rotational, vibrational, agitational, centrifugal or planetary in nature.

It has been observed in some cases that when ball miling mucoactive particles with additive material, a fine powder is not produced. Instead the powder was compacted on the walls of the mill by the action of the mill. That has inhibited the milling action and prevented the preparation of the composite active particles. That problem occurred particularly when certain additive materials were used, in cases where the additive material was present in small proportions (typically <2%), in cases where the milling balls were relatively small (typically <3 mm), in cases where the milling speed was too slow and where the starting particles were too fine. To prevent this occurring it is advantageous to ball mill in a liquid medium. The liquid medium reduces the tendency to compaction, assists the dispersal of additive material and improves any milling action.

The liquid medium may be high or low volatility and of any solid content as long as it does not dissolve the mucoactive particles to any significant degree and its viscosity is not so high that it prevents effective milling. The liquid medium preferably is not aqueous. The liquid is preferably one in which the additive material is substantially insoluble but some degree of solubility may be acceptable as long as there is sufficient additive material present that undissolved particles of additive material remain. Suitable liquid media include diethylether, acetone, cyclohexane, ethanol, isopropanol or dichloromethane. Liquid media are preferred which are non-flammable, for example dichloromethane and fluorinated hydrocarbons, especially fluorinated hydrocarbons which are suitable for use as propellants in inhalers.

The results of spray drying heparin and jet milling heparin with an FCA (heparin+leucine (95:5)) are set out below in Table 1.

TABLE 1

Particle size study of spray dried and jet milled heparin with FCA

| Formulation | d(10) | d(50) | d(60) | d(90) | Yield % | FPD <5 µm |
|---|---|---|---|---|---|---|
| Spray dried collected from cyclone | 1.2 | 2.7 | 3.3 | 7.2 | 55 | 37.4 |
| Spray dried collected from cyclone | 0.4 | 0.9 | 1.1 | >100 | 15 | 25.0 |
| Spray dried collected from cyclone and then jet milled | 1.1 | 2.6 | 3.1 | 5.9 | | 40.2 |
| Spray dried 6.5 hr | | | | | 75 | |
| Jet milled 1x | 0.85 | 3.4 | 4.2 | 8.8 | | 20.4 |
| Jet milled 2x | 0.95 | 3.5 | 4.1 | 7 | | 37.1 |
| Jet milled 3x | 1.1 | 2.8 | 3.3 | 5.5 | | 41.0 |
| Jet milled heparin 1x | | | | | | 7.0 |
| Pure heparin | | | | | | 12.0 |

Heparin and leucine (95:5) in a 2% (w/w) solution was spray dried using an SL10 spray drier, with a conventional two-fluid atomiser. The powder was spray dried at a temperature of 250° C. and a nozzle air pressure of 80 psi. The liquid flow rate used was 32 ml/min.

The resulting powder was collected in a cyclone. This powder was then secondary dried under vacuum. The powder was then filled into capsules at 20 mg, and then fired from a Monohaler device into a twin stage impinger. The resulting FPF(MD) was 37%. The FPF(MD) increased to 40% following a subsequent air jet milling of the powder to reduce any solid bridges between particles in agglomerates. The powder was also analysed by Malvern particle sizer.

The combination of heparin and leucine (95:5) was also air jet milled using a Hosokawa Micron AS50 mill. The material was passed twice through the mill. The powder was also analysed by Malvern particle sizer.

The d(50) value and the FPF(MD) were similar to the results achieved in the above spray dried powders.

Pure heparin powder was air jet milled with two passes and gave an FPF(MD) of only 7%. The d(50) of this powder is substantially larger than that of the leucine containing air jet milled sample.

In a further example, a USN was used to prepare dry powders using a feed solution of an active agent (heparin) alone, and a blend of active agent with 1% to 5% and 10% w/w FCA (l-leucine). The ultrasonic nebuliser output rate was 130 ml/hr. The furnace temperature of the nebulised powders was set at 350° C. FIG. 2 shows a schematic drawing of the ultrasonic set-up.

In order to test the processing of the powders, work was conducted using a Monohaler and a capsule filled with 20 mg powder and fired into a rapid TSI in the manner explained previously. The study used a TSI flow rate of 60 l pm with a cut-off of approximately 5 µm.

Three measurements were made for each blend and the results are summarised below, giving the average values of the three sets of results obtained.

TABLE 2

Rapid TSI results using the dry powder produced using a USN with varying amounts of FCA

| Formulation | FPF % (metered dose) | FPD (mg) |
|---|---|---|
| Heparin (0% leucine) | 1.1 | 0.22 |
| Heparin + leucine (1% w/w) | 17.4 | 3.5 |
| Heparin + leucine (2% w/w) | 30.2 | 6.0 |
| Heparin + leucine (3% w/w) | 28.6 | 5.7 |
| Heparin + leucine (4% w/w) | 48.4 | 9.7 |
| Heparin + leucine (5% w/w) | 41.5 | 8.3 |
| Heparin + leucine (10% w/w) | 55.8 | 11.8 |

The rapid TSI results using the dry powder produced using the USN indicate a very low aerosolisation efficiency for pure heparin particles, but an improvement appeared in FPF with addition of l-leucine as a FCA.

In a particle size study, the particle size of the spray dried particles formed using the USN was analysed. The dry powders were dispersed at 4 bar in Sympatec particle sizer (Helos dry dispersed). The values of d(10), d(50) and d(90) of the ultrasonic nebulised powders were measured and are indicated in the table below (10% by volume of the particles are of a size, measured by Sympatec, that is below the d(10) value, 50% by volume of the particles are of a size, measured by Sympatec, that is below the d(50) value and so on). The values are an average of three measurements.

In addition, the percentage mass of particles with a size of less than 5 µm was obtained from the particle size data and is expressed as FPF.

TABLE 3

Particle size study of spray dried particles using USN

| Formulation | d(10) (μm) | d(50) (μm) | d(90) (μm) | FPF % (<5 μm) |
|---|---|---|---|---|
| Heparin (0% leucine) | 0.43 | 1.07 | 4.08 | 90.52 |
| Heparin + leucine (1% w/w) | 0.41 | 0.90 | 1.79 | 99.97 |
| Heparin + leucine (2% w/w) | 0.41 | 0.89 | 1.75 | 100 |
| Heparin + leucine (3% w/w) | 0.41 | 0.88 | 1.71 | 100 |
| Heparin + leucine (4% w/w) | 0.41 | 0.86 | 1.71 | 100 |
| Heparin + leucine (5% w/w) | 0.41 | 0.90 | 1.84 | 100 |
| Heparin + leucine (10% w/w) | 0.41 | 0.89 | 1.76 | 100 |

It can be seen that particles formed using a spray drying process involving an ultrasonic nebuliser have been found to have a greater FPF than those produced using a standard spray drying apparatus, for example with a two-fluid nozzle configuration.

What is more, the particles formed using a spray drying process using a USN have been found to have a narrower particle size distribution than those produced using a standard spray drying apparatus, for example with a two-fluid nozzle configuration.

Clearly there are other known techniques for forming fine particles comprising a mucoactive agent and a FCA. Such techniques include, for example, techniques using supercritical fluids (SCFs), which have been explored for many years for particle production purposes. Similar to the spray-drying technique, this technique provides a direct formation of micron-sized particles suitable for inhalation powders. The most commonly used supercritical fluid technologies for particle production are rapid expansion of supercritical solutions (RESS) and supercritical antisolvent (SAS) or gas antisolvent (GAS) methods.

RESS is based on a rapid expansion of a SCF. The process involves dissolving the drug mixture in a SCF, followed by a rapid expansion of the fluid causing the compound to precipitate. This technique is capable of producing uniform particles, with control on the size distribution and morphology of particles. However, this technique is limited by the fact that most drugs have low solubility in the SCFs.

SAS is a recrystallisation process that relies on the capability of SCFs to act as an antisolvent to precipitate particles within a liquid solution. Unlike in the RESS technique, SAS does not require a high solubility of the drug compounds in the SCFs. Therefore, SAS is more commercially viable for powder production.

Recently a solution enhanced dispersion by supercritical fluids (SEDS) was introduced, see for example patent publications GB 2322326, WO 95/01324, WO 95/01221, U.S. Pat. No. 5,851,453 and WO 96/00610. This technique is based on simultaneous dispersion, solvent extraction and particle formation in a highly turbulent flow. SEDS is capable of generating uncharged and crystalline product, with the capability of controlling particle size and size distribution by manipulating process conditions.

Another approach is the technique known as emulsion precipitation. This method can be used to prepare fine particles of mucoactive agent and one or more FCAs.

An experimental programme was conducted to test the mucolytic activity of selected mucoactive agents. The primary objective of this initial protocol is to determine the mucolytic activity (capacity to reduce the viscosity and elasticity and thereby affect clearability) of heparin in cystic fibrosis sputum at concentrations of potential clinical relevance. This constitutes the Stage 1 experiment, below. The secondary objective is to compare heparin with other heparin fractions in a screening test for activity, incorporated in the Stage 2 experiment.

The experiments were carried out using a protocol similar to that described by Sun et al. (Sun F, Tai S, Lim T, Baumann U, King M (2002) "Additive effect of dornase alfa and Nacystelyn on transportability and viscoelasticity of cystic fibrosis sputum" Can Respir J, 9: 401-406). In Stage 1, several concentrations of heparin were investigated, and the results will be compared with vehicle control (normal 0.15M saline) and a control (Nacystelyn). Sputum samples were collected from adult patients with cystic fibrosis.

The magnetic microrheometer was described by King (King M (1988) "Magnetic microtheometer" Methods in Bronchial Mucology, pp. 73-83.). This instrument is used to measure the bulk viscosity and elasticity of microliter quantities of mucus. A 100 μm steel ball is carefully positioned in a 1-10 μL sample of mucus and oscillated by means of an electromagnetic field gradient. The motion of this sphere is tracked with the aid of a photocell. Plots of ball displacement versus magnetic force are used to determine the viscosity and elasticity of the mucus as a function of applied frequency (1-100 rad/s). These theological properties can be used to predict the effectiveness of mucus in clearance, both by ciliary action and for clearance by airflow interaction. This instrument is particularly suited to the proposed studies involving multiple treatments of sputum because of the minimal sample requirement.

Frog palate studies of mucociliary clearance were also used in the studies. The frog palate epithelium is lined with cilia and secretes and clears mucus much the same as the mammalian trachea. Mucociliary clearance continues at a steady rate for several hours after sacrifice and excision of the palate (King M, Festa E (1998) "The evolution of the frog palate model for mucociliary clearance" Cilia, Mucus and Mucociliary Interactions, pp. 191-201). During this period, the rate of palatal mucociliary clearance can be modulated by agents that alter the ciliary activity or that change the properties of the superficial fluid layer (mucus and periciliary fluid). By waiting longer (1-2 days in the bullfrog), mucus secretion ceases while ciliary activity continues for at least 5-6 days. During this extended period, mucus from endogenous or exogenous (e.g. cystic fibrosis) sources or mucus simulants are transported at rates that are reflective of their viscoelastic properties.

Mucociliary velocity (MCV) were measured by observing the rate of movement of endogenous mucus, using a calibrated macroscope and a stopwatch. MCV is computed as the distance of marker particle travel divided by elapsed time (mm/s). A mean of five consecutive runs for each test solution are used to compute each value of MCV.

When interpreting the results of the studies discussed herein, the primary variable of interest is the decrease in mucus viscoelasticity, expressed as delta log G* (corrected for vehicle treatment). A significant decrease in log G* at a given concentration of heparin is taken as evidence supporting mucolytic activity. Mucociliary clearability (rate of clearance of mucolytic-treated sputum relative to vehicle-treated sputum) is a second variable of interest. Mucolytic treatments that reduce the degree of crosslinking without destroying the basic mucous gel structure should result in an improvement in in vitro clearability.

Stage 1 (Heparin Dose-Response)

From each of 10 CF sputum samples, up to 6 aliquots of approximately 10-15 mg each were incubated for 30 minutes at 37° with either 0.9% NaCl or with one of the concentrations of heparin, or with N-acetylcysteine L-lysinate (NAL) (309 mcg/mL). Prior to incubation and following it, sputum viscoelasticity at 10 rad/s was determined by magnetic microrheometry. The mucolytic effect of each solution is defined by the mean fractional decrease in G* (vector sum of viscosity and elasticity) over the 10 samples tested.

The results are summarized in FIG. 3. It can be seen from the graph that the agents tested exhibited the desired activity and act as mucoactive agents. Furthermore, whilst the'lowest dose of heparin has little effect, the activity of the heparin is dose dependent and increased doses are clearly effective and will assist mucus clearance. It is also of note that the NAL was effective at a lower concentration compared to heparin.

Stage 2 (Heparin Fractions and/or Heparin Formulation)

Figure 4:
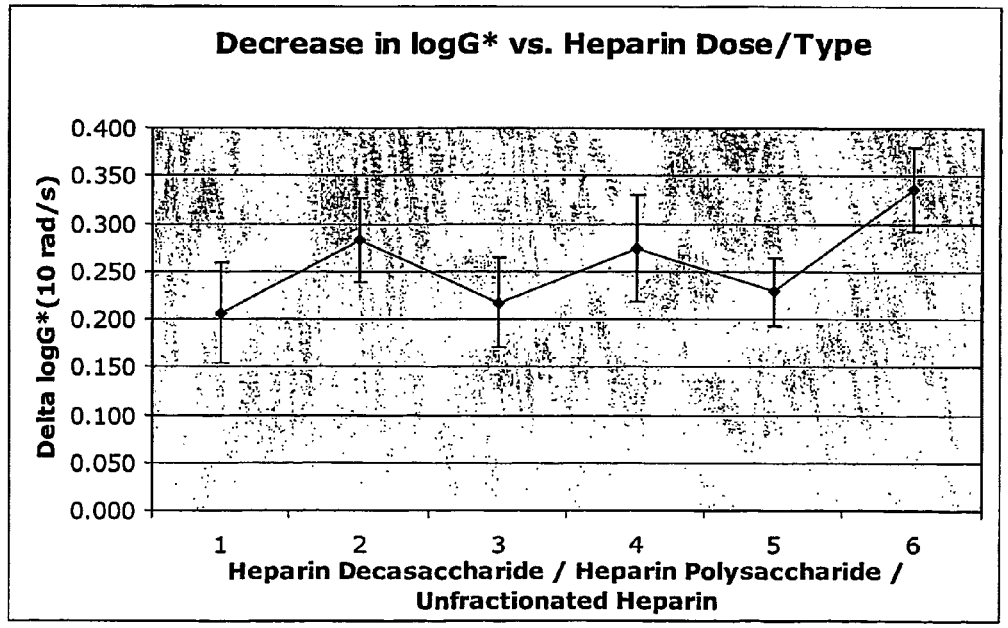
FIG. 4 Graph showing the effect of administration of various heparin preparations to CF sputum samples, as measured by the decrease in G* (vector sum of viscosity and elasticity of sputum). Samples 1 and 2 are heparin disaccharide at 1.6 mg/mL and 5 mg/mL respectively, samples 3 and 4 are heparin polysaccharide at 1.6 mg/mL and 5 mg/mL respectively, and samples 5 and 6 are unfractionated heparin at 1.6 mg/mL and 5 mg/mL respectively.

The design of this experiment was similar to Stage 1, except for the use of heparin size fractions and Nacystelyn control. The results are shown in FIG. 4.

Data points 1 and 2 are for heparin decasacharride, points 3 and 4 are for heparin polysaccharide, and points 5 and 6 are for unfractionated heparin each at 1.6 mg/mL and 5 mg/mL respectively.

The results show there is little difference in theological effect of the two heparin fractions versus the original unfractionated heparin. Each of them results in a dose-dependent mucolytic effect, i.e. a decrease in log G* that's greater for 5 mg/mL than for 1.6 mg/mL. At 5 mg/mL, the decrease in log G* for the original unfractionated heparin is a little greater than for the two new preparations.

The dry powder compositions of the present invention are preferably delivered by an inhaler device, most preferably by a dry powder inhaler (DPI). This type of inhaler is commonly used for pulmonary administration of a dry powder formulation. Thus, according to a further aspect of the invention, a DPI is provided, for dispensing the composition of the present invention.

The DPI may include a reservoir for holding the powder formulation and a metering mechanism for metering out individual doses of the formulation from the reservoir. Examples of such devices include Turbohaler (trademark) (AstraZeneca) or Clickhaler (trademark) (Innovata Biomed Ltd).

Alternatively, the dry powder inhaler may be arranged to use pre-metered doses of the formulation packaged, for example, in hard or soft gelatin capsules or blister packs. The Rotahaler (trademark) (GlaxoSmithKline), Spinhaler (trademark) (Rhône-Poulenc Rorer), Cyclohaler (trademark) (Pharmachemie B.V.) and Monohaler (trademark) (Miat) are examples of this type of dry powder inhaler. The invention also provides a metered dose of the formulation contained, for example, in a hard or soft gelatin capsule or blister pack. The aforementioned devices are passive devices, but active devices, such as an Aspirair (trademark) device (see WO 01/00262 and GB 2353222) may also be used.

Preferably, the inhaler is arranged to dispense one or more doses of the formulation, each dose comprising an effective amount of one or more mucoactive agents to be made available for inhalation. The dose may comprise not mote than 250 mg of one or more mucoactive agents, preferably not more than 100 mg, more preferably not more than 50 mg and most preferably not more than 20 mg of one or more mucoactive agents. The dose may comprise at least 5 mg of one or more mucoactive agents, preferably at least 20 mg, more preferably at least 50 mg. A preferred dose comprises 70-80 mg one or more mucoactive agents.

In another embodiment of the present invention, the DPI is adapted to deliver one or more mucoactive agents to the deep lung of a patient at a dose of at least 5,000 IU.

According to another aspect of the present invention, a package is provided for use in a DPI containing as amount of the composition which comprises at least 20 mg of one or more mucoactive agents. Preferably, the DPI according to the invention is arranged to use a package according to the invention.

According to a yet further aspect of the present invention, the compositions according to the invention are used for use in therapy. Preferably, they are for use in treating pulmonary diseases which involve excess mucus in the airways or problems clearing mucus from the airways, examples of which are discussed above.

The invention claimed is:

1. A method of treating a pulmonary disease comprising the administration of a therapeutically effective amount of a pharmaceutical composition to a subject in need of such treatment, wherein the pulmonary disease has as a symptom the excess formation of mucus secretions in the airways, said pulmonary disease is selected from the group consisting of chronic bronchitis, acute asthma, cystic fibrosis, chronic obstructive pulmonary disease and bronchiectasis, said composition comprising one or more mucoactive agents which assist mucous clearance through one or more of the following mechanisms: reducing cross-linking within the mucus, diluting the mucus, and digesting naked DNA and cell debris within the mucus, wherein the composition is a dry powder and comprises heparin and 2% or more w/w of leucine.

2. The method of claim 1, wherein one or more of the mucoactive agents are able to reduce inflammation.

3. The method of claim 1, comprising two or more mucoactive agents.

4. The method of claim 1, wherein the composition further comprises a heparinoid.

5. The method of claim 4, wherein the heparinoid is one or more of the following: danaparoid sodium and dermatan sulphate.

6. The method of claim 4, wherein the heparinoid contains heparin, dermatan sulphate and chondroitin sulphate.

7. The method of claim 1, wherein the dry powder further comprises one or more of: a monosaccharide, a disaccharide, and an oligosaccharide.

8. The method of claim 1, wherein the dry powder further comprises one or more of: dextran, dextrin, glucose and mannitol.

9. The method of claim 1, wherein the dry powder further comprises one or more of: rhDNase, gelsolin and thymosin g4.

10. The method of claim 1, wherein the dry powder further comprises one or more of: acetylcysteine and Nacystelyn.

11. The method of claim 1, wherein the composition is a dry powder for pulmonary inhalation.

12. The method of claim 11, wherein the composition has a fine particle fraction of at least 50%, fine particle fraction being the percentage mass of particles with a size of less than 5 μm.

13. The method of claim 11, wherein the composition has a fine particle fraction of between 50 and 90%.

14. The method of claim 11, wherein the composition comprises fine particles of the one or more mucoactive agents, which have upon their surfaces an amount of the leucine as a force control agent.

15. The method of claim 14, wherein an additional force control agent is selected from the group consisting of: an amino acid peptide, a phospholipid and a metal stearate.

16. The method of claim 15, wherein an additional force control agent is selected from the group consisting of: lysine, cysteine, and mixtures thereof.

17. The method of claim 14, wherein the force control agent is included in an amount of up to 50% w/w.

18. The method of claim 11, wherein the composition comprises particles of mucoactive agent having a mass median aerodynamic diameter of less than 10 μm.

19. The method of claim 18, wherein the particles of mucoactive agent have a mass median aerodynamic diameter of from about 2 to about 5 μm.

20. The method of claim 11, wherein the composition further comprises carrier particles.

21. The method of claim 1, for the treatment of a human patient in need of such therapy.

22. A method of producing particles for use in a composition as claimed in claim 1, the method comprising spray drying the one or more mucoactive agents in a spray drier.

23. A method as claimed in claim 22, wherein the step of spray drying further includes producing droplets moving at a controlled velocity.

24. A method as claimed in claim 23, wherein the velocity of droplets at 5 mm from their point of generation is less than 20 m/s.

25. A method as claimed in claim 23, wherein the spray drier comprises an ultrasonic nebuliser.

26. A method as claimed in claim 23, wherein the heparin is co-spray dried with the leucine.

27. A method of producing particles for use in a composition as claimed in claim 1, the method comprising the step of jet milling particles of the heparin in the presence of an element selected from the group consisting of: air, a compressible gas, and a fluid.

28. A method as claimed in claim 27, wherein the particles are jet milled in the presence of the leucine.

29. A method as claimed in claim 27, wherein the step of jet milling is carried out at an inlet pressure of between 0.1 and 3 bar.

30. A method as claimed in claim 27, wherein the step of jet milling is carried out at an inlet pressure of between 3 and 12 bar.

31. A method as claimed in claim 27, wherein at least 90% by volume of the active particles are less than 20 μm in diameter prior to jet milling.

32. A method as claimed in claim 22, wherein 90% of the resulting dried particles have a size of less than 10 μm, as measured by laser diffraction.

33. The method of claim 11, wherein said composition has a fine particle fraction of between 70 and 99%.

34. The method of claim 11, wherein said composition has a fine particle fraction of between 80 and 99%.

35. The method of claim 11, wherein said composition has a fine particle fraction of between 60 and 70%.

36. The method of claim 14, wherein the force control agent is included in an amount of less than 10% w/w.

37. The method of claim 14, wherein the force control agent is included in an amount of less than 5% w/w.

38. The method of claim 11, wherein the carrier particles have a particle size of at least 20 μm.

39. The method of claim 1, wherein the composition comprises 2% to 10% w/w of leucine.

40. The method of claim 1, wherein the composition comprises 2% to 70% w/w of leucine.

41. A composition for assisting mucus clearance, the composition comprising heparin and 2% or more w/w of leucine, wherein the composition is dry powder for pulmonary inhalation and assists mucus clearance through one or more of the following mechanisms: reducing cross-linking within the mucus, diluting the mucus; and/or digesting naked DNA and cell debris within the mucus.

42. The composition as claimed in claim 41, wherein the composition comprises 2% to 10% w/w of leucine.

* * * * *